United States Patent [19]

Fukuda et al.

[11] Patent Number: 5,684,134
[45] Date of Patent: Nov. 4, 1997

[54] ANTIBODY SPECIFIC FOR β1→6 N-ACETYLGLUCOSAMININYLTRANSFERASE

[75] Inventors: Minoru Fukuda; Marti F. A. Bierhuizen, both of San Diego, Calif.

[73] Assignee: La Jolla Cancer Research Center, La Jolla, Calif.

[21] Appl. No.: 487,069

[22] Filed: Jun. 7, 1995

Related U.S. Application Data

[60] Continuation of Ser. No. 227,455, Apr. 14, 1994, which is a division of Ser. No. 955,041, Oct. 1, 1992, Pat. No. 5,360,733.

[51] Int. Cl.$^6$ .................. C07K 16/40; C07K 16/06; C12N 9/10
[52] U.S. Cl. .................. 530/388.26; 435/193; 435/338; 530/389.1
[58] Field of Search ................... 435/193, 240.27; 530/389.1, 388.26

[56] References Cited

U.S. PATENT DOCUMENTS 5,360,733  11/1994  Fukuda et al. ................ 435/193
5,484,590  1/1996  Fukuda ........................ 424/94.5

OTHER PUBLICATIONS

Oehrlein, Reinhold et al., "Use of the core-2 –N–acetylglucosaminyltransferase in the Chemical-Enzymatic Synthesis of a Sialy–Le$^x$-containing Hexasaccharide Found on O–linked Glycoproteins." Carbohydrate Res. 244:149–159 (1993).

Pallant, Adam et al., "Characterization of cDNAs Encoding Human Leukosialin and Localization of the Leukosialin Gene to Chromosome 16." Proc. Natl. Acad. Sci. USA 86:1332–1338 (1989).

Shelley, C. Simon. "Molecular Characterization of Sialophorin (CD43), the Lymphocyte Surface Sialoglycoprotein Defective in Wiskott-Aldrich Syndrome." Proc. Natl. Acad. Sci. USA 86:2819–2823 (1989).

Kudo, Shinichi and Fukuda, Minoru., "A Short, Novel Promoter Sequence Confers the Expression of Human Leukosialin, a Major Sialoglycoprotein on Leukocytes." J. Biol. Chem. 266:8483–8486 (1991).

Ropp, Philip A., "Mucin Biosynthesis: Purification and Characterization of a Mucin βN–Acetylglucosaminyltransferase." J. Biol. Chem. 266:23863–23871 (1991).

Kawashima, Hiroto, et al., "Purification and Characterization of UDP–GlcNAc:Galβ1–4Glc (NAc) β–1,3–N–Acetylglucosaminyltransferase (Poly-N-acetyllactosamine Extension Enzyme) from Calf Serum." J. Biol. Chem. 268:27118–27126 (1993).

Fox, Robert I. et al., "A Novel Cell Surface Antigen (T305) Found in Increased Frequency on Acute Leukemia Cells and in Autoimmune Disease States." J. Immun. 131:762–767 (1983).

Saitoh, Osamu, et al., "T–Lymphocytic Leukemia Expresses Complex, Branched O–linked Oligosaccharides on a Major Sialoglycoprotein, Leukosialin." Blood 77:1491–1499 (1991).

Bierhuizen, Marti F. and Fukuda, Minoru, "Expression Cloning of a cDNA Encoding UDP–GlcNAc:Galβ1–3–GalNAc-R (GlcNAc to GalNAc) β1–6GlcNAc Transferase by Hene Transfer into CHO Cells Expressing Polyoma Large Tumor Antigen." Proc. Natl. Acad. Sci. USA. 89:9326–9330 (1992).

Stern, David F. et al., "Spk1, a New Kinase from Saccharomyces Cerevisiae, Phosphorylates Proteins on Serine, Threonine, and Throsine." Mole. Cell. Biol. 11:987–1001 (1991).

Kornbluth, Sally, et al., "Novel Tyrosine Kinase Identified by Phosphotyrosine Antibody Screening of cDNA Libraries." Mole. Cell. Biol. 8:5541–5544 (1988).

Toone, Eric J. et al., "Tetrahedron Report No. 259: Enzyme--catalyzed Synthesis of Carbohydrates." Tetrahedron. 45:5365–5422 (1989).

Piller, Friedrich, et al., "Altered O–Glycan Synthesis in Lymphocytes from Patients with Wiskott-Aldrich Syndrome." J. Exp. Med. 173:1501–1510 (1991).

Schachter, Harry, "Enzymes Associated with Glycosylation." Current Opinion Struct. Biol. 1:755–765 (1991).

Heffernan, Michael and Dennis, James W. "Polyoma and Hamster Papovavirus Large T Antigen–Mediated Replication of Expression Shuttle Vectors in Chinese Hamster Ovary Cells." Nucleic Acids Res. 19:85–92 (1991).

Kukowska-Latallo, Jolanta F. et al., "A Cloned Human cDNA Determines Expression of a Mouse Stage-Specific Embryonic Antigen and the Lewis Blood Group α(1,3/1,4)Fucosyltransferase." Genes and Development 4:1288–1303 (1990).

Lowe, John B. et al., "ELAM–1–Dependent Cell Adhesion to Vascular Endothelium Determined by a Transfected Human Fucosyltransferase cDNA." Cell. 475–484 (1990).

Fukuda, Minoru et al., "Structures of O–linked Oligosaccharides Isolated from Normal Granulocytes, Chronic Myelogenous Leukemia Cells and Acute Myelogenous Leukemia Cells." J. Biol. Chem. 261:12796–12806 (1986).

Primary Examiner—Thomas M. Cunningham
Assistant Examiner—Martha T. Lubet
Attorney, Agent, or Firm—Campbell & Flores, LLP

[57] ABSTRACT

The present invention provides a novel β1→6 N-acetylglucosaminyltransferase, which forms core 2 oligosaccharide structures in O-glycans, and a novel acceptor molecule, leukosialin, CD43, for core 2 β1→6 N-acetylglucosaminyltransferase activity. The amino acid sequences and nucleic acid sequences encoding these molecules, as well as active fragments thereof, also are disclosed. A method for isolating nucleic acid sequences encoding proteins having enzymatic activity is disclosed, using CHO cells that support replication of plasmid vectors having a polyoma virus origin of replication. A method to obtain a suitable cell line that expresses an acceptor molecule also is disclosed.

4 Claims, 8 Drawing Sheets

```
                TTGGGACCACAAATGCAAAGGAAACCACCTCCCCTCCCCACCTCCCTCCTCTGCACCCTT    -299
                GAGTTCTCAGGCTCACATTCCCACCACCACCCTCTGAGCCCAGCCCTCCCTAGCATCACC    -239
Exon1'          ACTTCCATCCCATTCCTCAGCCAAGAGCCAGGAATCCTGATTCCAGATCCCACGCTTCCC    -179
                TGCCTCCCTCAGGTGAGCCCCAGACCCCCAGGCCCCTGGGAGCAGGGGTCAGGATGGAGGGGT    -119
                GATGGTGTCTTCGCCCAGCAGCTGTGGGAGCAGGCGGGTGGGGCAGGATGGAGGGGT    -59
                GGGTGGGGTGGGAGCCAGGGCCCACTTCCCTTTCCCCTTGGGGCCCTGTCCTTCCCAG      2
Exon1           TCTTGCCCCAGCCCTCGGAGGTGGTGGAGTGACCTGGCCCAGTGCTGCGTCCTTATCAG    62
                CCGAGCCGGTAAGAGGGTGAGACTTGGTGGGGTAGGGCCTCAGTGGGCCTGGGAATGTG    122
                CCTGTGGCTTGAAAAGACTCTGACAGGTTATGATGGAGAAGAGATTGGGAGCCATTGGCT    182
                GCACAGGGTCAGGGAAGGCCAGGGAAGGCCTCACTGCTAAGCTCTGGAATCTAAGCTGGGCT    242
                TGGAGGGAGCCTCAGGATGGGGTCAGGATGGGGAGCTGCCAGCATCTGTTCCTCTGTCATT    302
                TCTGATAACAGTAAAAGCCAGAGAGGGGAGGCCCGGAAAAAACCGTTAAACCAGGTCCTCCGGCCG    362
                TTGGCAGGGAAGTGGGCAGAGAGGGGAGGCCCGGCAACTCCCGGCCG    422
                CTGCTTCTCCGGCTGCCCACCTGCAGGTCCCAGCTCTTGCTCCTGCTGTTTGCCTGGAA    482
Exon2           ATGGCCACGCTTCTCCTTCCTTGGGGTGCTGGTGTAAGCCCAGAGACGCTCTGGGGAGC    542
                 M  A  T  L  L  L  L  L  G  V  L  V  V  S  P  D  A  L  G  S     (20)
```

```
CCTCTCTTTTCTGGCAGTGCCTACTTCGTGGTCAGTAGGGAGTATGTGGGGTATGTACTACAGAATGAAAAAATCCAAAAGTTGATGGAGTGGGCACAAGACACATACAGCCCTGATGAG    960
 P  L  F  S  G  S  A  Y  F  V  V  S  R  E  Y  V  G  Y  V  L  Q  N  E  K  I  Q  K  L  M  E  W  A  Q  D  T  Y  S  P  D  E   320

TATCTCTGGGCCACCATCCAAAGGATTCCTGAAGTCCCGGGCTCACTCCCTGCCAGCCATAAGTATGATCTATCTGACATGCAAGCAGTTGCCAGGTTTGTCAAGTGGCAGTACTTTGAG    1080
 Y  L  W  A  T  I  Q  R  I  P  E  V  P  G  S  L  P  A  S  H  K  Y  D  L  S  D  M  Q  A  V  A  R  F  V  K  W  Q  Y  F  E   360

GGTGATGTTTCCAAGGGTGCTCCCTACCCGCCTTGCGATGGAGTCCATGTGCGCTCAGTGTGCATTTGAACTGGTGACTGAAGGTGACTTGAACTGGATGCTGCGCAAACACCACTTGTTTGCCAAT    1200
 G  D  V  S  K  G  A  P  Y  P  P  C  D  G  V  H  V  R  S  V  C  I  F  G  A  G  D  L  N  W  M  L  R  K  H  H  L  F  A  N   400

AAGTTTGACGTGGACGTGTTGACCTCTTTGGCCATCCAGTGTTTGGATGAGCATTTGAGACACAAAGCTTTGGAGACATTTAAAACACTGAAGCAATTTATGAACAAGAAGAAGG    1320
 K  F  D  V  D  V  L  F  A  I  Q  C  L  D  E  H  L  R  H  K  A  L  E  T  L  K   H end                                    428

ATACACAAAACGTACCTTATCTGTTTCCCCTTCCTTGTCAGAGCTCGGGAAGATGGTATGAAGTCCTCTAGTAGATCTTCTTGTCAGAGAAGCTGCATGGTTTCT    1440

GCAGAGCACAGTTAGCTAGAAAGGTCTAGAAATGTTGATAGCATTAAATGTTCATCTAGAGTTAAAGGTAAAGGTAGCCTTGAGGCCAGAGCAGGTAGCAAGGCATTGTGGAAAGAGGGGAC    1560

CAGGGTGGCTGGGGAGAGGGCCGATGCATAAAGTCAGCCTGTTTCCAAGTGCTCAGGGACTTAGCAGAAGATGTGACCTGTGCCAAAACTATTTTGAGAATTTTAAATGTGACCA    1680

TTTTTCTGGTATGAATAAACTTACAGCAACAAATAATCAAAGATACAATTAATCTGATATTATATATTGAAATAGAAATTTGATTGTACTATATAAATGATTTTTGTAAATAATTTATAT    1800

TCTGCTCTAATACTGTACTGTGTAGTGTGTCTCCGTATGTCATCTCAGGGAGCTTAAAATGGGCTTGATTTAACATTGAAAAAAAA    1886
```

FIG. 5B

SEQUENCE LISTING ( 1 ) GENERAL INFORMATION:

( i i i ) NUMBER OF SEQUENCES: 8

( 2 ) INFORMATION FOR SEQ ID NO:1:

( i ) SEQUENCE CHARACTERISTICS:
    ( A ) LENGTH: 900 base pairs
    ( B ) TYPE: nucleic acid
    ( C ) STRANDEDNESS: both
    ( D ) TOPOLOGY: linear ( i i ) MOLECULE TYPE: DNA (genomic)

( i x ) FEATURE:
    ( A ) NAME/KEY: CDS
    ( B ) LOCATION: 841..900

( i x ) FEATURE:
    ( A ) NAME/KEY: exon
    ( B ) LOCATION: 91..192
    ( D ) OTHER INFORMATION: /note="EXON 1' IS LOCATED IN BOTH
         GENOMIC AND cDNA. IN THE cDNA EXON 1' IS
         IMMEDIATELY FOLLOWED BY EXON 2."

( i x ) FEATURE:
    ( A ) NAME/KEY: exon
    ( B ) LOCATION: 359..428
    ( D ) OTHER INFORMATION: /note="EXON 1 IS LOCATED IN
         GENOMIC DNA"

( i x ) FEATURE:
    ( A ) NAME/KEY: intron
    ( B ) LOCATION: 193..806
    ( D ) OTHER INFORMATION: /note="THIS SEGMENT OF NUCLEIC
         ACID CONSTITUTES INTRON SEQUENCE OF THE cDNA"

( i x ) FEATURE:
    ( A ) NAME/KEY: exon
    ( B ) LOCATION: 807..900
    ( D ) OTHER INFORMATION: /note="EXON 2 IS LOCATED IN BOTH
         GENOMIC AND cDNA. IN THE cDNA EXON 2 IMMEDIATELY
         FOLLOWS EXON 1'."

( x i ) SEQUENCE DESCRIPTION: SEQ ID NO:1:

```
TTGGGGACCA  CAAATGCAAA  GGAAACCACC  CTCCCCTCCC  ACCTCCTCCT  CTGCACCCTT      60
GAGTTCTCAG  GCTCACATTC  CCACCACCCA  CCTCTGAGCC  CAGCCCTCCC  TAGCATCACC     120
ACTTCCATCC  CATTCCTCAG  CCAAGAGCCA  GGAATCCTGA  TTCCAGATCC  CACGCTTCCC     180
TGCCTCCCTC  AGGTGAGCCC  CAGACCCCCA  GGCACCCCGC  TGGCCCCTGA  AGGAGCAGGT     240
GATGGTGCTG  TCTTCGCCCA  GCAGCTGTGG  GAGCAGGCGG  GTGGGCAGG   ATGGAGGGT     300
GGGTGGGGTG  GGTGGAGCCA  GGGCCCACTT  CCTTTCCCCT  TGGGGCCCTG  TCCTTCCCAG     360
TCTTGCCCCA  GCCTCGGGAG  GTGGTGGAGT  GACCTGGCCC  CAGTGCTGCG  TCCTTATCAG     420
CCGAGCCGGT  AAGAGGGTGA  GACTTGGTGG  GGTAGGGCC   TCAGTGGGCC  TGGGAATGTG     480
CCTGTGGCTT  GAAAAGACTC  TGACAGGTTA  TGATGGGAAG  AGATTGGGAG  CCATTGGGCT     540
GCACAGGGTC  AGGGAAGGCC  AGGAGGGGCT  GGTCACTGCT  GGAATCTAAG  CTGCTGAGGC     600
TGGAGGGAGC  CTCAGGATGG  GGCTGATGGG  GGAGCTGCCA  GCATCTGTTC  CTCTGTCATT     660
TCTGATAACA  GTAAAAGCCA  GCATGGAAAA  AACCGTTAAA  CCGCAGGTTG  GGCCTGGCCG     720
TTGGCAGGGA  AGTGGGCAGA  GGGGAGGCCC  GGCCAGGTCC  TCCGGCAACT  CCCGCGTGTT     780
CTGCTTCTCC  GGCTGCCCAC  CTGCAGGTCC  CAGCTCTTGC  TCCTGCCTGT  TTGCCTGGAA     840

ATG GCC ACG CTT CTC CTT CTC CTT GGG GTG CTG GTG GTA AGC CCA GAC           888
Met Ala Thr Leu Leu Leu Leu Leu Gly Val Leu Val Val Ser Pro Asp
```

```
                1               5                      10                    15
GCT CTG GGG AGC                                                                           900
Ala Leu Gly Ser
            20
```

( 2 ) INFORMATION FOR SEQ ID NO:2:

( i ) SEQUENCE CHARACTERISTICS:
        ( A ) LENGTH: 20 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met Ala Thr Leu Leu Leu Leu Leu Gly Val Leu Val Val Ser Pro Asp
 1               5                      10                    15

Ala Leu Gly Ser
            20
```

( 2 ) INFORMATION FOR SEQ ID NO:3:

( i ) SEQUENCE CHARACTERISTICS:
        ( A ) LENGTH: 2105 base pairs
        ( B ) TYPE: nucleic acid
        ( C ) STRANDEDNESS: both
        ( D ) TOPOLOGY: linear ( i i ) MOLECULE TYPE: cDNA ( i x ) FEATURE:
        ( A ) NAME/KEY: CDS
        ( B ) LOCATION: 220..1504

( i x ) FEATURE:
        ( A ) NAME/KEY: polyA_signal
        ( B ) LOCATION: 1913..1918

( i x ) FEATURE:
        ( A ) NAME/KEY: misc_signal
        ( B ) LOCATION: 248..314
        ( D ) OTHER INFORMATION: /standard_name=
            " SIGNAL/MEMBRANE-ANCHORING DOMAIN"

( x i ) SEQUENCE DESCRIPTION: SEQ ID NO:3:

```
GTGAAGTGCT CAGAATGGGG CAGGATGTCA CCTGGAATCA GCACTAAGTG ATTCAGACTT        60

TCCTTACTTT TAAATGTGCT GCTCTTCATT TCAAGATGCC GTTGCAGCTC TGATAAATGC       120

AAACTGACAA CCTTCAAGGC CACGACGGAG GGAAAATCAT TGGTGCTTGG AGCATAGAAG       180

ACTGCCCTTC ACAAAGGAAA TCCCTGATTA TTGTTTGAA ATG CTG AGG ACG TTG         234
                                            Met Leu Arg Thr Leu
                                             1                 5

CTG CGA AGG AGA CTT TTT TCT TAT CCC ACC AAA TAC TAC TTT ATG GTT        282
Leu Arg Arg Arg Leu Phe Ser Tyr Pro Thr Lys Tyr Tyr Phe Met Val
            10                  15                      20

CTT GTT TTA TCC CTA ATC ACC TTC TCC GTT TTA AGG ATT CAT CAA AAG        330
Leu Val Leu Ser Leu Ile Thr Phe Ser Val Leu Arg Ile His Gln Lys
        25                  30                  35

CCT GAA TTT GTA AGT GTC AGA CAC TTG GAG CTT GCT GGG GAG AAT CCT        378
Pro Glu Phe Val Ser Val Arg His Leu Glu Leu Ala Gly Glu Asn Pro
            40                  45                  50

AGT AGT GAT ATT AAT TGC ACC AAA GTT TTA CAG GGT GAT GTA AAT GAA        426
Ser Ser Asp Ile Asn Cys Thr Lys Val Leu Gln Gly Asp Val Asn Glu
        55                  60                  65

ATC CAA AAG GTA AAG CTT GAG ATC CTA ACA GTG AAA TTT AAA AAG CGC        474
Ile Gln Lys Val Lys Leu Glu Ile Leu Thr Val Lys Phe Lys Lys Arg
 70                  75                  80                  85
```

| | | | | | | | | | | | | | | | | |
|---|---|---|---|---|---|---|---|---|---|---|---|---|---|---|---|---|
| CCT | CGG | TGG | ACA | CCT | GAC | GAC | TAT | ATA | AAC | ATG | ACC | AGT | GAC | TGT | TCT | 522 |
| Pro | Arg | Trp | Thr | Pro | Asp | Asp | Tyr | Ile | Asn | Met | Thr | Ser | Asp | Cys | Ser | |
| | | 90 | | | | | | 95 | | | | | | 100 | | |
| TCT | TTC | ATC | AAG | AGA | CGC | AAA | TAT | ATT | GTA | GAA | CCC | CTT | AGT | AAA | GAA | 570 |
| Ser | Phe | Ile | Lys | Arg | Arg | Lys | Tyr | Ile | Val | Glu | Pro | Leu | Ser | Lys | Glu | |
| | | | 105 | | | | | 110 | | | | | 115 | | | |
| GAG | GCG | GAG | TTT | CCA | ATA | GCA | TAT | TCT | ATA | GTG | GTT | CAT | CAC | AAG | ATT | 618 |
| Glu | Ala | Glu | Phe | Pro | Ile | Ala | Tyr | Ser | Ile | Val | Val | His | His | Lys | Ile | |
| | 120 | | | | | 125 | | | | | 130 | | | | | |
| GAA | ATG | CTT | GAC | AGG | CTG | CTG | AGG | GCC | ATC | TAT | ATG | CCT | CAG | AAT | TTC | 666 |
| Glu | Met | Leu | Asp | Arg | Leu | Leu | Arg | Ala | Ile | Tyr | Met | Pro | Gln | Asn | Phe | |
| | 135 | | | | 140 | | | | | 145 | | | | | | |
| TAT | TGC | GTT | CAT | GTG | GAC | ACA | AAA | TCC | GAG | GAT | TCC | TAT | TTA | GCT | GCA | 714 |
| Tyr | Cys | Val | His | Val | Asp | Thr | Lys | Ser | Glu | Asp | Ser | Tyr | Leu | Ala | Ala | |
| 150 | | | | | 155 | | | | 160 | | | | | 165 | | |
| GTG | ATG | GGC | ATC | GCT | TCC | TGT | TTT | AGT | AAT | GTC | TTT | GTG | GCC | AGC | CGA | 762 |
| Val | Met | Gly | Ile | Ala | Ser | Cys | Phe | Ser | Asn | Val | Phe | Val | Ala | Ser | Arg | |
| | | | | 170 | | | | | 175 | | | | | 180 | | |
| TTG | GAG | AGT | GTG | GTT | TAT | GCA | TCG | TGG | AGC | CGG | GTT | CAG | GCT | GAC | CTC | 810 |
| Leu | Glu | Ser | Val | Val | Tyr | Ala | Ser | Trp | Ser | Arg | Val | Gln | Ala | Asp | Leu | |
| | | | 185 | | | | | 190 | | | | | 195 | | | |
| AAC | TGC | ATG | AAG | GAT | CTC | TAT | GCA | ATG | AGT | GCA | AAC | TGG | AAG | TAC | TTG | 858 |
| Asn | Cys | Met | Lys | Asp | Leu | Tyr | Ala | Met | Ser | Ala | Asn | Trp | Lys | Tyr | Leu | |
| | | 200 | | | | | 205 | | | | | 210 | | | | |
| ATA | AAT | CTT | TGT | GGT | ATG | GAT | TTT | CCC | ATT | AAA | ACC | AAC | CTA | GAA | ATT | 906 |
| Ile | Asn | Leu | Cys | Gly | Met | Asp | Phe | Pro | Ile | Lys | Thr | Asn | Leu | Glu | Ile | |
| | 215 | | | | | 220 | | | | | 225 | | | | | |
| GTC | AGG | AAG | CTC | AAG | TTG | TTA | ATG | GGA | GAA | AAC | AAC | CTG | GAA | ACG | GAG | 954 |
| Val | Arg | Lys | Leu | Lys | Leu | Leu | Met | Gly | Glu | Asn | Asn | Leu | Glu | Thr | Glu | |
| 230 | | | | | 235 | | | | | 240 | | | | | 245 | |
| AGG | ATG | CCA | TCC | CAT | AAA | GAA | GAA | AGG | TGG | AAG | AAG | CGG | TAT | GAG | GTC | 1002 |
| Arg | Met | Pro | Ser | His | Lys | Glu | Glu | Arg | Trp | Lys | Lys | Arg | Tyr | Glu | Val | |
| | | | | 250 | | | | | 255 | | | | | 260 | | |
| GTT | AAT | GGA | AAG | CTG | ACA | AAC | ACA | GGG | ACT | GTC | AAA | ATG | CTT | CCT | CCA | 1050 |
| Val | Asn | Gly | Lys | Leu | Thr | Asn | Thr | Gly | Thr | Val | Lys | Met | Leu | Pro | Pro | |
| | | | 265 | | | | | 270 | | | | | 275 | | | |
| CTC | GAA | ACA | CCT | CTC | TTT | TCT | GGC | AGT | GCC | TAC | TTC | GTG | GTC | AGT | AGG | 1098 |
| Leu | Glu | Thr | Pro | Leu | Phe | Ser | Gly | Ser | Ala | Tyr | Phe | Val | Val | Ser | Arg | |
| | | 280 | | | | | 285 | | | | | 290 | | | | |
| GAG | TAT | GTG | GGG | TAT | GTA | CTA | CAG | AAT | GAA | AAA | ATC | CAA | AAG | TTG | ATG | 1146 |
| Glu | Tyr | Val | Gly | Tyr | Val | Leu | Gln | Asn | Glu | Lys | Ile | Gln | Lys | Leu | Met | |
| | 295 | | | | | 300 | | | | | 305 | | | | | |
| GAG | TGG | GCA | CAA | GAC | ACA | TAC | AGC | CCT | GAT | GAG | TAT | CTC | TGG | GCC | ACC | 1194 |
| Glu | Trp | Ala | Gln | Asp | Thr | Tyr | Ser | Pro | Asp | Glu | Tyr | Leu | Trp | Ala | Thr | |
| 310 | | | | | 315 | | | | | 320 | | | | | 325 | |
| ATC | CAA | AGG | ATT | CCT | GAA | GTC | CCG | GGC | TCA | CTC | CCT | GCC | AGC | CAT | AAG | 1242 |
| Ile | Gln | Arg | Ile | Pro | Glu | Val | Pro | Gly | Ser | Leu | Pro | Ala | Ser | His | Lys | |
| | | | | 330 | | | | | 335 | | | | | 340 | | |
| TAT | GAT | CTA | TCT | GAC | ATG | CAA | GCA | GTT | GCC | AGG | TTT | GTC | AAG | TGG | CAG | 1290 |
| Tyr | Asp | Leu | Ser | Asp | Met | Gln | Ala | Val | Ala | Arg | Phe | Val | Lys | Trp | Gln | |
| | | | 345 | | | | | 350 | | | | | 355 | | | |
| TAC | TTT | GAG | GGT | GAT | GTT | TCC | AAG | GGT | GCT | CCC | TAC | CCG | CCC | TGC | GAT | 1338 |
| Tyr | Phe | Glu | Gly | Asp | Val | Ser | Lys | Gly | Ala | Pro | Tyr | Pro | Pro | Cys | Asp | |
| | | 360 | | | | | 365 | | | | | 370 | | | | |
| GGA | GTC | CAT | GTG | CGC | TCA | GTG | TGC | ATT | TTC | GGA | GCT | GGT | GAC | TTG | AAC | 1386 |
| Gly | Val | His | Val | Arg | Ser | Val | Cys | Ile | Phe | Gly | Ala | Gly | Asp | Leu | Asn | |
| | 375 | | | | | 380 | | | | | 385 | | | | | |
| TGG | ATG | CTG | CGC | AAA | CAC | CAC | TTG | TTT | GCC | AAT | AAG | TTT | GAC | GTG | GAT | 1434 |
| Trp | Met | Leu | Arg | Lys | His | His | Leu | Phe | Ala | Asn | Lys | Phe | Asp | Val | Asp | |
| 390 | | | | | 395 | | | | | 400 | | | | | 405 | |

```
GTT GAC CTC TTT GCC ATC CAG TGT TTG GAT GAG CAT TTG AGA CAC AAA    1482
Val Asp Leu Phe Ala Ile Gln Cys Leu Asp Glu His Leu Arg His Lys
                410                 415                 420

GCT TTG GAG ACA TTA AAA CAC T GACCATTACG GGCAATTTTA TGAACAAGAA    1534
Ala Leu Glu Thr Leu Lys His
                425

GAAGGATACA CAAAACGTAC CTTATCTGTT TCCCCTTCCT TGTCAGCGTC GGGAAGATGG    1594
TATGAAGTCC TCTTTGGGGC AGGGACTCTA GTAGATCTTC TTGTCAGAGA AGCTGCATGG    1654
TTTCTGCAGA GCACAGTTAG CTAGAAAGGT GATAGCATTA AATGTTCATC TAGAGTTAAT    1714
AGTGGGAGGA GTAAAGGTAG CCTTGAGGCC AGAGCAGGTA GCAAGGCATT GTGGAAAGAG    1774
GGGACCAGGG TGGCTGGGGA AGAGGCCGAT GCATAAAGTC AGCCTGTTCC AAGTGCTCAG    1834
GGACTTAGCA AAATGAGAAG ATGTGACCTG TGCCAAAACT ATTTGAGAA TTTTAAATGT    1894
GACCATTTTT CTGGTATGAA TAAACTTACA GCAACAAATA ATCAAGATA CAATTAATCT    1954
GATATTATAT TTGTTGAAAT AGAAATTTGA TTGTACTATA AATGATTTTT GTAAATAATT    2014
TATATTCTGC TCTAATACTG TACTGTGTAG TGTGTCTCCG TATGTCATCT CAGGGAGCTT    2074
AAAATGGGCT TGATTTAACA TTGAAAAAAA A                                   2105
```

( 2 ) INFORMATION FOR SEQ ID NO:4:

( i ) SEQUENCE CHARACTERISTICS:
        ( A ) LENGTH: 428 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

```
Met Leu Arg Thr Leu Leu Arg Arg Arg Leu Phe Ser Tyr Pro Thr Lys
 1               5                  10                  15

Tyr Tyr Phe Met Val Leu Val Leu Ser Leu Ile Thr Phe Ser Val Leu
                20                  25                  30

Arg Ile His Gln Lys Pro Glu Phe Val Ser Val Arg His Leu Glu Leu
                35                  40                  45

Ala Gly Glu Asn Pro Ser Ser Asp Ile Asn Cys Thr Lys Val Leu Gln
            50                  55                  60

Gly Asp Val Asn Glu Ile Gln Lys Val Lys Leu Glu Ile Leu Thr Val
 65                 70                  75                  80

Lys Phe Lys Lys Arg Pro Arg Trp Thr Pro Asp Asp Tyr Ile Asn Met
                85                  90                  95

Thr Ser Asp Cys Ser Ser Phe Ile Lys Arg Arg Lys Tyr Ile Val Glu
                100                 105                 110

Pro Leu Ser Lys Glu Glu Ala Glu Phe Pro Ile Ala Tyr Ser Ile Val
            115                 120                 125

Val His His Lys Ile Glu Met Leu Asp Arg Leu Leu Arg Ala Ile Tyr
    130                 135                 140

Met Pro Gln Asn Phe Tyr Cys Val His Val Asp Thr Lys Ser Glu Asp
145                 150                 155                 160

Ser Tyr Leu Ala Ala Val Met Gly Ile Ala Ser Cys Phe Ser Asn Val
                165                 170                 175

Phe Val Ala Ser Arg Leu Glu Ser Val Val Tyr Ala Ser Trp Ser Arg
            180                 185                 190

Val Gln Ala Asp Leu Asn Cys Met Lys Asp Leu Tyr Ala Met Ser Ala
        195                 200                 205
```

| Asn | Trp | Lys | Tyr | Leu | Ile | Asn | Leu | Cys | Gly | Met | Asp | Phe | Pro | Ile | Lys |
| 210 | | | | | 215 | | | | | 220 | | | | | |

| Thr | Asn | Leu | Glu | Ile | Val | Arg | Lys | Leu | Lys | Leu | Leu | Met | Gly | Glu | Asn |
| 225 | | | | | 230 | | | | | 235 | | | | | 240 |

| Asn | Leu | Glu | Thr | Glu | Arg | Met | Pro | Ser | His | Lys | Glu | Glu | Arg | Trp | Lys |
| | | | | 245 | | | | | 250 | | | | | 255 | |

| Lys | Arg | Tyr | Glu | Val | Val | Asn | Gly | Lys | Leu | Thr | Asn | Thr | Gly | Thr | Val |
| | | | 260 | | | | | 265 | | | | | 270 | | |

| Lys | Met | Leu | Pro | Pro | Leu | Glu | Thr | Pro | Leu | Phe | Ser | Gly | Ser | Ala | Tyr |
| | | 275 | | | | | 280 | | | | | 285 | | | |

| Phe | Val | Val | Ser | Arg | Glu | Tyr | Val | Gly | Tyr | Val | Leu | Gln | Asn | Glu | Lys |
| | 290 | | | | | 295 | | | | | 300 | | | | |

| Ile | Gln | Lys | Leu | Met | Glu | Trp | Ala | Gln | Asp | Thr | Tyr | Ser | Pro | Asp | Glu |
| 305 | | | | | 310 | | | | | 315 | | | | | 320 |

| Tyr | Leu | Trp | Ala | Thr | Ile | Gln | Arg | Ile | Pro | Glu | Val | Pro | Gly | Ser | Leu |
| | | | | 325 | | | | | 330 | | | | | 335 | |

| Pro | Ala | Ser | His | Lys | Tyr | Asp | Leu | Ser | Asp | Met | Gln | Ala | Val | Ala | Arg |
| | | | 340 | | | | | 345 | | | | | 350 | | |

| Phe | Val | Lys | Trp | Gln | Tyr | Phe | Glu | Gly | Asp | Val | Ser | Lys | Gly | Ala | Pro |
| | | 355 | | | | | 360 | | | | | 365 | | | |

| Tyr | Pro | Pro | Cys | Asp | Gly | Val | His | Val | Arg | Ser | Val | Cys | Ile | Phe | Gly |
| | 370 | | | | | 375 | | | | | 380 | | | | |

| Ala | Gly | Asp | Leu | Asn | Trp | Met | Leu | Arg | Lys | His | His | Leu | Phe | Ala | Asn |
| 385 | | | | | 390 | | | | | 395 | | | | | 400 |

| Lys | Phe | Asp | Val | Asp | Val | Asp | Leu | Phe | Ala | Ile | Gln | Cys | Leu | Asp | Glu |
| | | | | 405 | | | | | 410 | | | | | 415 | |

| His | Leu | Arg | His | Lys | Ala | Leu | Glu | Thr | Leu | Lys | His |
| | | | 420 | | | | | 425 | | | |

( 2 ) INFORMATION FOR SEQ ID NO:5:

( i ) SEQUENCE CHARACTERISTICS:
        ( A ) LENGTH: 34 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:5:

TTTGAATTCC CCTGAATTTG TAAGTGTCAG ACAC        34

( 2 ) INFORMATION FOR SEQ ID NO:6:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:6:

TTTGAATTCG CAGAAACCAT GCAGCTTCTC TGA        33

( 2 ) INFORMATION FOR SEQ ID NO:7:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear (  i  i  )  MOLECULE TYPE: protein (  v  )  FRAGMENT TYPE: internal (  i  x  )  FEATURE:
                   ( A ) NAME/KEY: CDS
                   ( B ) LOCATION: 1..15
                   ( D ) OTHER INFORMATION: /note="PROTEIN A - C2GNT FUSION
                        PROTEIN"

(  x  i  )  SEQUENCE DESCRIPTION: SEQ ID NO:7:

```
GGG  AAT  TCC  CCT  GAA                                                      15
Gly  Asn  Ser  Pro  Glu
 1                    5
```

( 2 ) INFORMATION FOR SEQ ID NO:8:

(  i  )  SEQUENCE CHARACTERISTICS:
                   ( A ) LENGTH: 5 amino acids
                   ( B ) TYPE: amino acid
                   ( D ) TOPOLOGY: linear (  i  i  )  MOLECULE TYPE: protein (  x  i  )  SEQUENCE DESCRIPTION: SEQ ID NO:8:

```
Gly  Asn  Ser  Pro  Glu
 1                    5
```

ANTIBODY SPECIFIC FOR β1→6 N-ACETYLGLUCOSAMININYLTRANSFERASE

This application is a continuation of application Ser. No. 08/227,455, filed Apr. 14, 1994, now pending, which is a divisional of application Ser. No. 07/955,041, filed Oct. 1, 1992, now U.S. Pat. No. 5,360,733, on Nov. 1, 1994.

This work was supported by grants CA33000 and CA33895 awarded by the National Cancer Institute. The United States Government has certain rights in this invention.

BACKGROUND OF THE INVENTION

1. Field of the Invention

This invention relates generally to the fields of biochemistry and molecular biology and more specifically to a novel human enzyme, UDP-GlcNAc:Galβ1→3GalNAc (GlcNAc to GalNAc) β1→6 N-acetylgtucosaminyltransferase (core 2 β1→6 N-acetylglucosaminyltransferase; C2GnT; EC2.4.1.102), and to a novel acceptor molecule, leukosialin, CD43, for core 2 β1→6 N-acetylglucosaminyltransferase action. The invention additionally relates to DNA sequences encoding core 2 β1→6 N-acetylglucosaminyltransferase and leukosialin, to vectors containing a C2GnT DNA sequence or a leukosialin DNA sequence, to recombinant host cells transformed with such vectors and to a method of transient expression cloning in CHO cells for identifying and isolating DNA sequences encoding specific proteins, using CHO cells expressing a suitable acceptor molecule.

BACKGROUND INFORMATION

Most O-glycosidic oligosaccharides in mammalian glycoproteins are linked via N-acetylgalactosamine to the hydroxyl groups of serine or threonine. These O-glycans can be classified into 4 different groups depending on the nature of the core portion of the oligosaccharides (see FIG. 1). Although less well studied than N-glycans, O-glycans likely have important biological functions. Indeed, the presence of O-linked oligosaccharides with the core 2 branch, Galβ1→3 (GlcNAcβ1→6)GalNAc, has been demonstrated in many biological processes.

Piller et al., *J. Biol. Chem.* 263: 15146–15150 (1988) reported that human T-cell activation is associated with the conversion of core 1-based tetrasaccharides to core 2-based hexasaccharides on leukosialin, a major sialoglycoprotein present on human T lymphocytes (see also FIG. 1). A similar increase in hexasaccharides was observed in peripheral blood lymphocytes of patients suffering from T-cell leukemias (Saitoh et al., *Blood* 77: 1491–1499 (1991)), myelogenous leukemias (Brockhausen et al., *Cancer Res.* 51: 1257–1263 (19911) and immunodeficiency due to AIDS and the Wiskott-Aldrich syndrome (Piller et al., *J. Exp. Med.* 173: 1501–1510 (1991)). In these patients' lymphocytes, changes in the amount of hexasaccharides were caused by increased activity of either UDP-GlcNAc:Galβ1→3GalNAc (GlcNAc to GalNAc) 6-β-D-N-acetylglucosaminyltransferase or core 2 β1→6 N-acetylglucosaminyltransferase (Williams et al., *J. Biol. Chem.* 255: 11253–11261 (1980)). Increased activity of core 2 β1→6 N-acetylglucosaminyltransferase also was observed in metastatic murine tumor cell lines as compared to their parental, non-metastatic counterparts (Yousefi et al., *J. Biol. Chem.* 266: 1772–1782 (1991)).

Increased complexity of the attached oligosaccharides increases the molecular weight of the glycoprotein. For example, leukosialin containing hexasaccharides has a molecular weight of ~135 kna, whereas leukosialin containing tetrasaccharides has a molecular weight of ~105 kDa (Carlsson et al., *J. Biol. Chem.* 261: 12779–12786 and 12787–12795 (1986)).

Fox et al., *J. Immunol.* 131: 762–767 (1983) raised a monoclonal antibody, T305, against human T-lymphocytic leukemia cells. Sportsman et al., *J. Immunol.* 135: 158–164 (1985) reported T305 binding was abolished by neuraminidase treatment, suggesting T305 binds to hexasaccharides. T305 specifically reacts with the high molecular weight form of leukosialin (Saitoh et al., supra, (1991)).

Previous studies indicated poly-N-acetyilactosamine repeats extend almost exclusively from the branch formed by the core 2 β1→6 N-acetylglucosaminyltransferase (Fukuda et al., *J. Biol. Chem.* 261: 12796–2806 (1986)). Consistent with these results, Yousefi et al., supra, (1991) demonstrated that the core 2 enzyme in metastatic tumor cells regulates the level of poly-N-acetyllactosamine synthesis in O-linked oligosaccharides.

Poly-N-acetyllactosamines are subject to a variety of modifications, including the formation of the sialyl Le$^x$, NeuNAcα2→3Galβ1→4(Fucα1→3)GlcNAc-, or the sialyl Le$^a$, NeuNAcα2→3Galβ1→3 (Fucα1→4)GlcNAc-, determinants (Fukuda, *Biochim. Biophys. Acta* 780: 119–150 (1985)). Such modifications are significant because these determinants, which are present on neutrophils and monocytes, serve as ligands for E- and P-selectin present on endothelial cells and platelets, respectively (see, for example, Larsen et al., *Cell* 63: 467–474 (1990)).

In addition, tumor cells often express a significant amount of sialyl Le$^x$ and/or sialyl Le$^a$ on their cell surfaces. The interaction between E-selectin or P-selectin and these cell surface carbohydrates may play a role in tumor cell adhesion to endothelium during the metastatic process (Walz et al., supra, (1990)). Kojima et al., *Biochem. Biophys. Res. Commun.* 182: 1288–1295 (1992) reported that selectin-dependent tumor cell adhesion to endothelial cells was abolished by blocking O-glycan synthesis. Complex sulfated O-glycans also may serve as ligands for the lymphocyte homing receptor, L-selectin (Imai et al., *J. Cell Biol.* 113: 1213–1221 (1991)).

These reported observations establish core 2 β1→6 N-acetylglucosaminyltransferase as a critical enzyme in O-glycan biosynthesis. The availability of core 2 β1→6 N-acetylglucosaminyltransferase will allow the in vivo and in vitro production of specific glycoprotein having core 2 oligosaccharides and subsequent study of these variant O-glycans on cell-cell interactions. For example, core 2 β1→6 N-acetylglucosaminyltransferase is a useful marker for transformed or cancerous cells. An understanding of the role of core 2 β1→6 N-acetylglucosaminyltransferase in transformed and cancerous cells may elucidate a mechanism for the aberrant cell-cell interactions observed in these cells. In order to understand the control of expression of these oligosaccharides and their function, isolation of a cDNA clone for core 2 β1→6 N-acetylglucosaminyltransferase is a prerequisite. However, the DNA sequence encoding core 2 β1→6 N-acetylglucosaminyltransferase has not yet been reported.

Thus, a need exists for identifying the core 2 β1→6 N-acetylglucosaminyltransferase and the DNA sequences encoding this enzyme. The present invention satisfies this need and provides related advantages as well.

SUMMARY OF THE INVENTION

The present invention generally relates to a novel purified human β1→6 N-acetylglucosaminyltransferase. A cDNA sequence encoding a 428 amino acid protein having β1→6 N-acetylglucosaminyltransferase activity also is provided. The purified human β1→6 N-acetylglucosaminyltransferase, or an active fragment thereof, catalyzes the formation of critical branches in O-glycans.

The invention further relates to a novel purified acceptor molecule, leukosialin, CD43, for core 2 β1→6 N-acetylglucosaminyltransferase activity. The leukosialin cDNA encodes a novel variant leukosialin, which is created by alternative splicing of the genomic leukosialin DNA sequence.

Isolated nucleic acids encoding either core 2 β1→6 N-acetylglucosaminyltransferase or leukosialin are disclosed, as are vectors containing the nucleic acids and recombinant host cells transformed with such vectors. The invention further provides methods of detecting such nucleic acids by contacting a sample with a nucleic acid probe having a nucleotide sequence capable of hybridizing with the isolated nucleic acids of the present invention. The core 2 β1→6 N-acetylglucosaminyltransferase and leukosialinamino acid and nucleic acid sequences disclosed herein can be purified from human cells or produced using well known methods of recombinant DNA technology.

The invention also discloses a method of isolating nucleic acid sequences encoding proteins that have an enzymatic activity. Such a nucleic acid sequence is obtained by transfecting the nucleic acid, which is contained within a vector having a polyoma virus replication origin, into a Chinese hamster ovary (CHO) cell line simultaneously expressing polyoma virus large T antigen and the acceptor molecule for the protein having an enzymatic activity.

BRIEF DESCRIPTION OF THE DRAWINGS

FIG. 2 depicts genomic DNA sequence (SEQ. ID. NO. 1) and cDNA sequence (SEQ. ID. NO. 2) of leukosialin. The genomic sequence is numbered relative to the transcriptional start site. Exon 1 and exon 2 have been previously described. Exon 1' is newly identified here. In the isolated cDNA, exon 1' is immediately followed by the exon 2 sequence. Deduced amino acids are presented under the coding sequence, which begins in exon 2 (SEQ. ID. NO. 3). A portion of the exon 2 sequence is shown.

In FIG. 3A, six clonal CHO cell lines were examined for replication of pcDNAI-based pGT/hCG (lanes 1–6).

FIG. 4D shows a phase micrograph of the same field shown in FIG. 4C. Bar=20 μm.

FIG. 5 depicts the cDNA sequence (SEQ. ID. NO. 4) and translated amino acid sequences (SEQ. In. NO. 5) of core 2 β1→6 N-acetylglucosaminyltransferase. The open reading frame and full-length nucleotide sequence of C2GnT are shown. The signal/membrane-anchoring domain is doubly underlined. The polyadenylation signal is boxed. Potential N-glycosylation sites are marked with asterisks. The sequences are numbered relative to the translation start site.

DETAILED DESCRIPTION OF THE INVENTION

Figure 1:
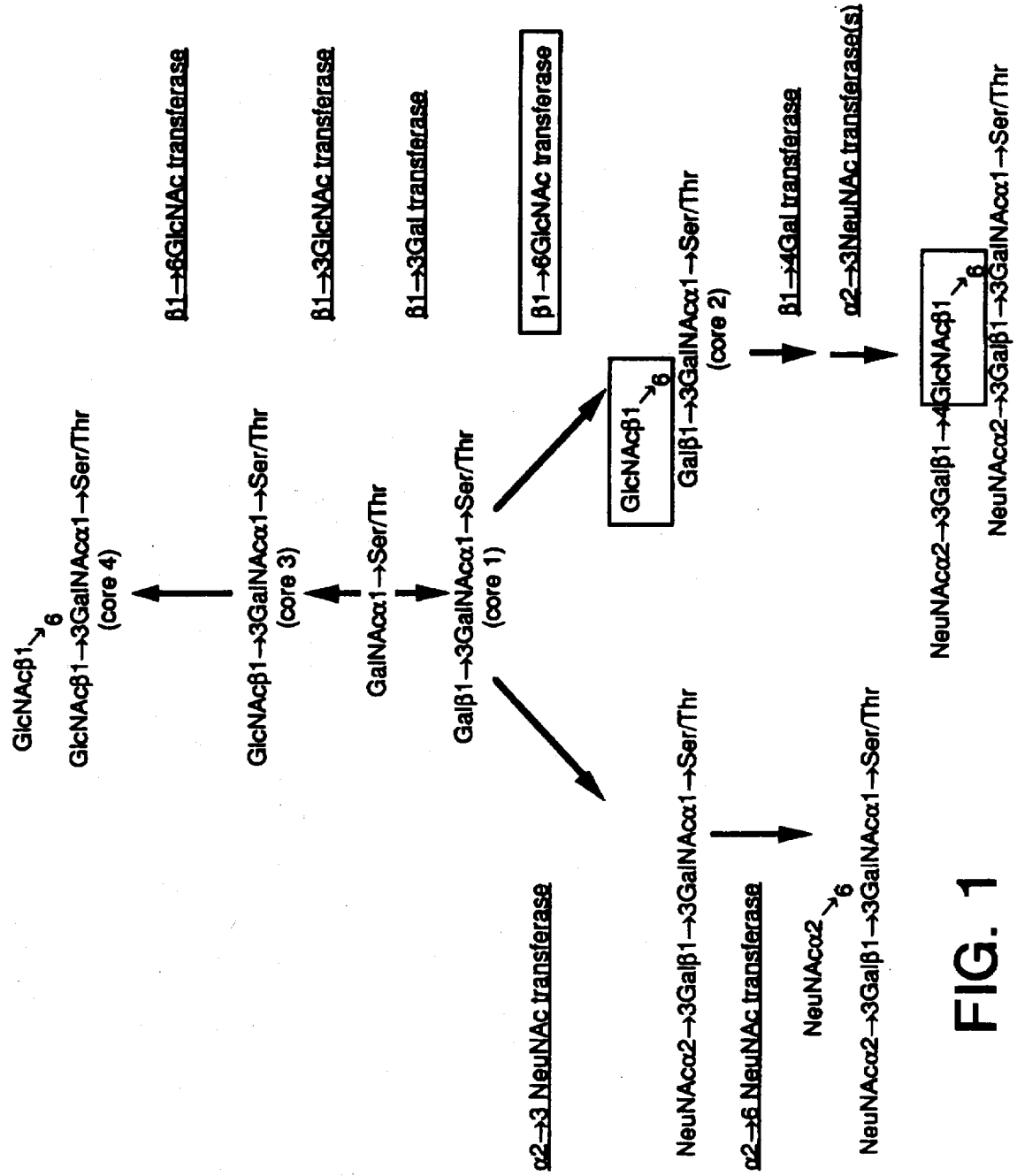
FIG. 1 depicts the structures and biosynthesis of O-glycans. Structures of O-glycan cores can be classified into 4 groups (core 1 to core 4), each of which is synthesized starting with GalNAcα1→Ser/Thr. The core 1 structure is synthesized by the addition of a β1→3 Gal residue to the GalNAc residue. The core 1 structure can be converted to core 2 by the addition of a β1→6 N-acetylglucosaminyl residue. This intermediate is usually converted to the hexasaccharide by sequential addition of galactose and sialic acid residues (bottom right). The core 2 β1→6 N-acetylglucosaminyltransferase and the linkage formed by the enzyme are indicated by a box. In certain cell types, the core 2 structure can be extended by the addition of N-acetyllactosamine (Galβ1→4GlcNAcβ1→3) repeats to form poly-N-acetyllactosamine. In the absence of core 2 β1→6 N-acetylglucosaminyltransferase, core 1 is converted to the monosialoform, then to the disialoform by sequential addition of α2→3- and α2→6-linked sialic acid residues (bottom left). Alternatively, core 3 can be synthesized by the addition of a β1→3 N-acetylglucosaminyl residue to the GalNAc residue. Core 3 can be converted to core 4 by another β1→6 N-acetylglucosaminyltransferase (top of figure).

The present invention generally relates to a novel human core 2 β1→6 N-acetylglucosaminyltransferase. The invention further relates to a novel method of transient expression cloning in CHO cells that was used to isolate the cDNA sequence encoding human core 2 β1→6 N-acetylglucosaminyltransferase (C2GnT). The invention also relates to a novel human leukosialin, which is an acceptor molecule for core 2 β1→6 N-acetylglucosaminyltransferase activity.

Cells generally contain extremely low amounts of glycosyltransferases. As a result, cDNA cloning based on screening using an antibody or a probe based on the glycosyltransferase amino acid sequence has met with limited success. However, isolation of cDNAs encoding various glycosyltransferases can be achieved by transient expression of cDNA in recipient cells.

Successful application of the transient expression cloning method to isolate a cDNA sequence encoding a glycosyltransferase requires an appropriate recipient cell line. Ideal recipient cells should not express the glycosyltransferase of interest. As a result, the recipient cells would normally lack the oligosaccharide structure formed by such a glycosyltransferase.

Expression of the cloned glycosyltransferase cDNA in the recipient cell line should result in formation of the specific oligosaccharide structure. The resultant oligosaccharide can be identified using a specific antibody or lectin that recognizes the structure. The recipient cell line also must support replication of an appropriate plasmid vector.

COS-1 cells initially appear to satisfy the requirements for using the transient expression method. COS-1 cells express SV40 large T antigen and support the replication of plasmid vectors harboring a SV40 replication origin (Gluzman et al., Cell 23: 175–182 (1981)). Although COS-1 cells, themselves, express a variety of glycosyltransferases, COS-1 cells have been used to clone cDNA sequences encoding human blood group Lewis α1→¾ fucosyltransferase and murine α1→3 galactosyltransferase (Kukowska-Latallo et al., Genes and Devel. 4: 1288–1303 (1990); Larsen et al., Proc. Natl. Acad. Sci. USA 86: 8227–8231 (1989)). Also, Goelz et al., Cell 63: 175–182 (1990), utilized an antibody that inhibits E-selectin mediated adhesion to isolate a cDNA sequence encoding α1→3 fucosyltransferase.

An attempt was made to use COS-1 cells to isolate cDNA clones encoding core 2 β1→6 N-acetylglucosaminyltransferase. COS-1 cells were transfected using cDNA obtained from activated human T cells, which express the core 2 β1→6 N-acetylglucosaminyltransferase. Transfected cells suspected of expressing core 2 β1→6 N-acetylglucosaminyltransferase in the transfected cells were identified by the presence of increased levels of the core 2 oligosaccharide structure formed by core 2 β1→6 N-acetylglucosaminyltransferase activity. The presence of the core 2 structure was identified using the monoclonal antibody, T305, which identifies a hexasaccharide on leukosialin. A clone expressing high levels of the T305 antigen was isolated and sequenced.

Surprisingly, transfection using COS-1 cells resulted in the isolation of a cDNA clone encoding a novel variant of human leukosialin, which is the acceptor molecule for core 2 β1→6 N-acetylglucosaminyltransferase activity. Examination of the cDNA sequence of the newly isolated leukosialin revealed the cDNA sequence was formed as a result of alternative splicing of exons in the genomic leukosialin DNA sequence. Specifically, the newly isolated leukosialin is encoded by cDNA sequence containing a previously undescribed non-coding exon at the 5'-terminus (exon 1' in FIG. 2; SEQ. ID. NO. 1 and SEQ. ID. NO. 2).

The unexpected result obtained using COS-1 cells led to the development of a new transfection system to isolate a cDNA sequence encoding core 2 β1→6 N-acetylglucosaminyltransferase. OHO cells, which do not normally express the T305 antigen, were transfected with DNA sequences encoding human leukosialin and the polyoma virus large T antigen. A cell line, designated CHO-Py-leu, which expresses human leukosialin and polyoma virus large T antigen, was isolated.

CHO-Py-leu cells were used for transient expression cloning of a cDNA sequence encoding core 2 β1→6 N-acetylglucosaminyltransferase. CHO-Py-leu cells were transfected with cDNA obtained from human HL-60 promyelocytes. A plasmid, pcDNAI-C2Gnt, which directed expression of the T305 antigen, was isolated and the cDNA insert was sequenced (see FIG. 5; SEQ. ID. NO. 4). The 2105 base pair cDNA Sequence encodes a putative 428 amino acid protein. The genomic DNA sequence encoding C2GmT can be isolated using methods well known to those skilled in the art, such as nucleic acid hybridization using the core 2 β1→6 N-acetylglucosaminyltransferase cDNA disclosed herein to screen, for example, a genomic library prepared from HL-60 promyelocytes.

An enzyme similar to the disclosed human core 2 β1→6 N-acetylglucosaminyltransferase has been purified from bovine tracheal epithelium (Ropp et al., J. Biol. Chem. 266: 23863–23871 (1991), which is incorporated herein by reference. The apparent molecular weight of the bovine enzyme is ~69 kDa. In comparison, the predicted molecular weight of the polypeptide portion of core 2 β1→6 N-acetylglucosaminyltransferase is ~50 kDa. The deduced amino acid sequence of core 2 β1→6 N-acetylglucosaminyltransferase reveals two to three potential N-glycosylation sites, suggesting N-glycosylation and O-glycosylation, or other post-translational modification, could account for the larger apparent size of the bovine enzyme.

Expression of the cloned C2GnT sequence, or a fragment thereof, directed formation of the specific O-glycan core 2 oligosaccharide structure. Although several cDNA sequences encoding glycosyltransferases have been isolated (Paulson and Colley, J. Biol. Chem. 264: 17615–17618 (1989); Schachter, Curr. Opin. Struct. Biol. 1: 755–765 (1991), which are incorporated herein by reference), C2GnT is the first reported cDNA sequence encoding an enzyme involved exclusively in O-glycan synthesis.

In O-glycans, β1→6 N-acetylglucosaminyl linkages may occur in both core 2, Galβ1→3(GlcNAcβ1→6)GalNAc, and core 4, GlcNAcβ1→3 (GlcNAcβ1→6)GalNAc, structures (Brockhausen et al., Biochemistry 24: 1866–1874 (1985), which is incorporated herein by reference. In addition, β1→6 N-acetylglucosaminyl linkages occur in the side chains of poly-N-acetyllactosamine, forming the i-structure (Piller et al., J. Biol. Chem. 259: 13385–13390 (1984), which is incorporated herein by reference), and in the side chain attached to α-mannose of the N-glycan core structure, forming a tetraantennary saccharide (Cummings et al., J. Biol. Chem. 257: 13421–13427 (1982), which is incorporated herein by reference). The enzymes responsible for these linkages all share the unique property that $Mn^{2+}$ is not required for their activity.

Although it was originally suggested that these β1→6 N-acetylglucosaminyl linkages were formed by the same enzyme (Piller at al., 1984), the present disclosure clearly demonstrates that the HL-60-derived core 2 β1→6 N-acetylglucosaminyltransferase is specific for the formation only of O-glycan core 2. This result is consistent with a recent report demonstrating that myeloid cell lysates contain the enzymatic activity associated with core 2, but not core 4, formation (Brockhausen et al., supra, (1991)).

Analysis of mRNA isolated from colonic cancer cells indicated core 2 β1→6 N-acetylglucosaminyltransferase is expressed in these cells. Recent studies using affinity absorption suggested at least two different β1→6 N-acetylglucosaminyltransferases were present in tracheal epithelium (Ropp et al., supra, (1991)). One of these transferases formed core 2, core 4, and I structures. Thus, at least one other β1→6 N-acetylglucosaminyltransferase present in epithelial cells can form core 2, core 4 and I structures. Similarly, a β1→6 N-acetylglucosaminyltransferase present in Novikoff hepatoma cells can form both core 2 and I structures (Koenderman et al., Eur. J. Biochem. 166: 199–208 (1987), which is incorporated herein by reference).

The acceptor molecule specificity of core 2 β1→6 N-acetylglucosaminyltransferase is different from the specificity of the enzymes present in tracheal epithelium and Novikoff hepatoma cells. Thus, a family of β1→6 N-acetylglucosaminyltransferases can exist, the members of which differ in acceptor specificity but are capable of forming the same linkage. Members of this family are isolated from cells expressing β1→6 N-acetylglucosaminyltransferase activity, using, for example, nucleic acid hybridization assays and studies of acceptor molecule specificity. Such a family was reported for the α1→3 fucosyltransferases (Weston et al., J. Biol. Chem. 267: 4152–4160 (1992), which is incorporated herein by reference).

The formation of the core 2 structure is critical to cell structure and function. For example, the core 2 structure is essential for elongation of poly-N-acetyllactosamine and for formation of sialyl Le$^x$ or sialyl Le$^a$ structures. Furthermore, the biosynthesis of cartilage keratan sulfate may be initiated by the core 2 β1→6 N-acetylglucosaminyltransferase, since the keratan sulfate chain is extended from a branch present in core 2 structure in the same way as poly-N-acetyllactosamine (Dickenson et al., Biochem. J. 269: 55–59 (1990), which is incorporated herein by reference). Keratan sulfate is absent in wild-type CHO cells, which do not express the core 2 β1→6 N-acetylglucosaminyltransferase (Esko et al., J. Biol. Chem. 261: 15725–15733 (1986), which is incorporated herein by reference). These structures are believed to be important for cellular recognition and matrix formation. The availability of the cDNA clone encoding the core 2 β1→6 N-acetylglucosaminyltransferase will aid in understanding how the various carbohydrate structures are formed during differentiation and malignancy. Manipulation of the expression of the various carbohydrate structures by gene transfer and gene inactivation methods will help elucidate the various functions of these structures.

The present invention is directed to a method for transient expression cloning in CHO cells of cDNA sequences encoding proteins having enzymatic activity. Isolation of human core 2 β1→6 N-acetylglucosaminyltransferase is provided as an example of the disclosed method. However, the method can be used to obtain cDNA sequences encoding other proteins having enzymatic activity.

For example, lectins and antibodies reactive with other specific oligosaccharide structures are available and can be used to screen for glycosyltransferase activity. Also, CHO cell lines that have defects in glycosylation have been isolated. These cell lines can be used to study the activity of the corresponding glycosyltransferase (Stanley, Ann. Rev. Genet. 18: 525–552 (1984), which is incorporated herein by reference). CHO cell lines also have been selected for various defects in cellular metabolism, loss of expression of cell surface molecules and resistance to cytotoxic drugs (see, for example, Malmström and Krieger, J. Biol. Chem. 266: 24025–24030 (1991); Yayon et al., Cell 64: 841–848 (1991), which are incorporated hereinby reference). The approach disclosed herein should allow isolation of cDNA sequences encoding the proteins involved in these various cellular functions.

As used herein, the terms "purified" and "isolated" mean that the molecule or compound is substantially free of contaminants normally associated with a native or natural environment. For example, a purified protein can be obtained from a number of methods. The naturally-occurring protein can be purified by any means known in the art, including, for example, by affinity purification with antibodies having specific reactivity with the protein. In this regard, anti-core 2 β1→6 N-acetylglucosaminyltransferase antibodies can be used to substantially purify naturally-occurring core 2 β1→6 N-acetylglucosaminyltransferase from human HL-60 promyelocytes.

Alternatively, a purified protein of the present invention can be obtained by well known recombinant methods, utilizing the nucleic acids disclosed herein, as described, for example, in Serook et al., Molecular Cloning: A Laboratory Manual 2d ed. (Cold Spring Harbor Laboratory 1989), which is incorporated herein by reference, and by the methods described in the Examples below. Furthermore, purified proteins can be synthesized by methods well known in the art.

As used herein, the phrase "substantially the sequence" includes the described nucleotide or amino acid sequence and sequences having one or more additions, deletions or substitutions that do not substantially affect the ability of the sequence to encode a protein have a desired functional activity. In addition, the phrase encompasses any additional sequence that hybridizes to the disclosed sequence under stringent hybridization sequences. Methods of hybridization are well known to those skilled in the art. For example, sequence modifications that do not substantially alter such activity are intended. Thus, a protein having substantially the amino acid sequence of FIG. 5 (SEQ. ID. NO. 5) refers to core 2 β1→6 N-acetylglucosaminyltransferase encoded by the cDNA described in Example IV, as well as proteins having amino acid sequences that are modified but, nevertheless, retain the functions of core 2 β1→6 N-acetylglucosaminyltransferase. One skilled in the art can readily determine such retention of function following the guidance set forth, for example, in Examples V and VI.

The present invention is further directed to active fragments of the human core 2 β1→6 N-acetylgiucosaminyttransferase protein. As used herein, an active fragment refers to portions of the protein that substantially retain the glycosyltransferase activity of the intact core 2 β1→6 N-acetylglucosaminyltransferase protein. One skilled in the art can readily identify active fragments of proteins such as core 2 β1→6 N-acetylglucosaminyltransferase by comparing the activities of a selected fragment with the intact protein following the guidance set forth in the Examples below.

As used herein, the term "glycosyltransferase activity" refers to the function of a glycosyltransferase to link sugar residues together through a glycosidic bond to create critical branches in oligosaccharides. Glycosyltransferase activity results in the specific transfer of a monosaccharide to an appropriate acceptor molecule, such that the acceptor molecule contains oligosaccharides having critical branches. One skilled in the art would understand the terms "enzymatic activity" and "catalytic activity" to generally refer to a function of certain proteins, such as the function of those proteins having glycosyltransferase activity.

As used herein, the term "acceptor molecule" refers to a molecule that is acted upon by a protein having enzymatic activity. For example, an acceptor molecule, such as leukosialin, as identified by the amino acid sequence of FIG. 2 (SEQ. ID. NO. 3), accepts the transfer of a monosaccharide due to glycosyltransferase activity. An acceptor molecule, such as leukosialin, may already contain one or more sugar residues. The transfer of monosaccharides to an acceptor molecule, such as leukosialin, results in the formation of critical branches of oligosaccharides.

As used herein, the term "critical branches" refers to oligosaccharide structures formed by specific glycosyltransferase activity. Critical branches may be involved in various cellular functions, such as cell-cell recognition. The oligosaccharide structure of a critical branch can be determined using methods well known in the art, such as the method for determining the core 2 oligosaccharide structure, as described in Examples V and VI.

Relatedly, the invention also provides nucleic acids encoding the human core 2 $\beta 1 \rightarrow 6$ N-acetylglucosaminyltransferase protein and leukosialin protein described above. The nucleic acids can be in the form of DNA, RNA or cDNA, such as the novel C2GnT cDNA of 2105 base pairs identified in FIG. 5 (SEQ. ID. NO. 4) or the novel leukosialin cDNA identified in FIG. 2 (SEQ. ID. NO. 2), for example. Such nucleic acids can also be chemically synthesized by methods known in the art, including, for example, the use of an automated nucleic acid synthesizer.

The nucleic acid can have substantially the nucleotide sequence of C2GnT, identified in FIG. 5 (SEQ. ID. NO. 4), or leukosialin identified in FIG. 2 (SEQ. ID. NO. 2). Portions of such nucleic acids that encode active fragments of the core 2 $\beta 1 \rightarrow 6$ N-acetylglucosaminyltransferase protein or leukosialin protein of the present invention also are contemplated.

Nucleic acid probes capable of hybridizing to the nucleic acids of the present invention under reasonably stringent conditions can be prepared from the cloned sequences or by synthesizing oligonucleotides by methods known in the art. The probes can be labeled with markers according to methods known in the art and used to detect the nucleic acids of the present invention. Methods for detecting such nucleic acids can be accomplished by contacting the probe with a sample containing or suspected of containing the nucleic acid under hybridizing conditions, and detecting the hybridization of the probe to the nucleic acid.

The present invention is further directed to vectors containing the nucleic acids described above. The term "vector" includes vectors that are capable of expressing nucleic acid sequences operably linked to regulatory sequences capable of effecting their expression. Numerous cloning vectors are known in the art. Thus, the selection of an appropriate cloning vector is a matter of choice. In general, useful vectors for recombinant DNA are often plasmids, which refer to circular double stranded DNA loops such as pcD-NAI or pcDSRG. As used herein, "plasmid" and "vector" may be used interchangeably as the plasmid is a common form of a vector. However, the invention is intended to include other forms of expression vectors that serve equivalent functions.

Suitable host cells containing the vectors of the present invention are also provided. Host cells can be transformed with a vector and used to express the desired recombinant or fusion protein. Methods of recombinant expression in a variety of host cells, such as mammalian, yeast, insect or bacterial cells are widely known. For example, a nucleic acid encoding core 2 $\beta 1 \rightarrow 6$ N-acetylglucosaminyltransferase or a nucleic acid encoding leukosialin can be transfected into cells using the calcium phosphate technique or other transfection methods, such as those described in Sambrook et al., supra, (1989).

Alternatively, nucleic acids can be introduced into cells by infection with a retrovirus carrying the gone or genes of interest. For example, the gone can be cloned into a plasmid containing retroviral long terminal repeat sequences, the C2Gnt DNA sequence or the leukosialin DNA sequence, and an antibiotic resistance gene for selection. The construct can then be transfected into a suitable cell line, such as PA12, which carries a packaging deficient provirus and expresses the necessary components for virus production, including synthesis of amphotrophic glycoproteins. The supernatant from these cells contain infectious virus, which can be used to infect the cells of interest.

Isolated recombinant polypeptides or proteins can be obtained by growing the described host cells under conditions that favor transcription and translation of the transfected nucleic acid. Recombinant proteins produced by the transfected host cells are isolated using methods set forth herein and by methods well known to those skilled in the art.

Also provided are antibodies having specific reactivity with the core 2 $\beta 1 \rightarrow 6$ N-acetylglucosaminyltransferase protein or leukosialin protein of the present invention. Active fragments of antibodies, for example, Fab and Fab'$_2$ fragments, having specific reactivity with such proteins are intended to fall within the definition of an "antibody." Antibodies exhibiting a liter of at least about $1.5 \times 10^5$, as determined by ELISA, are useful in the present invention.

The antibodies of the invention can be produced by any method known in the art. For example, polyclonal and monoclonal antibodies can be produced by methods described in Harlow and Lane, *Antibodies: A Laboratory Manual* (Cold Spring Harbor 1988), which is incorporated herein by reference. The proteins, particularly core 2 $\beta 1 \rightarrow 6$ N-acetylglucosaminyltransferase or leukosialin of the present invention can be used as immunogens to generate such antibodies. Altered antibodies, such as chimeric, humanized, CDR-grafted or bifunctional antibodies can also be produced by methods well known to those skilled in the art. Such antibodies can also be produced by hybridoma, chemical synthesis or recombinant methods described, for example, in Sambrook et al., supra, (1989).

The antibodies can be used for determining the presence or purification of the core 2 $\beta 1 \rightarrow 6$ N-acetylglucosaminyltransferase protein or the leukosialin protein of the present invention. With respect to the detecting of such proteins, the antibodies can be used for in vitro or in vivo methods well known to those skilled in the art.

Finally, kits useful for carrying out the methods of the invention are also provided. The kits can contain a core 2 $\beta 1 \rightarrow 6$ N-acetylglucosaminyltransferase protein, antibody or nucleic acid of the present invention and an ancillary reagent. Alternatively, the kit can contain a leukosialin protein, antibody or nucleic acid of the present invention and an ancillary reagent. An ancillary reagent may include diagnostic agents, signal detection systems, buffers, stabilizers, pharmaceutically acceptable carriers or other reagents and materials conventionally included in such kits.

A cDNA sequence encoding core 2 $\beta 1 \rightarrow 6$ N-acetylglucosaminyltransferase was isolated and core 2 $\beta 1 \rightarrow 6$ N-acetylglucosaminyltransferase activity was determined. This is the first report of transient expression cloning using CHO cells expressing polyoma large T antigen. The following examples are intended to illustrate but not limit the present invention.

EXAMPLE I

EXPRESSION CLONING IN COS-1 CELLS OF THE cDNA FOR THE PROTEIN CARRYING THE HEXASACCHARIDES

COS-1 cells were transfected with a cDNA library, pcDSRα-2F1, constructed from poly(A)$^+$ RNA of activated T lymphocytes, which express the core 2 β1→6 N-acetylglucosaminyltransferase (Yokota et al., *Proc. Natl. Acad. Sci. USA* 83: 5894–5898 (1986); Piller et al., supra, (1988), which are incorporated herein by reference). COS-1 cells support replication of the pcDSRα constructs, which contain the SV40 replication origin. Transfected cells were selected by panning using monoclonal antibody T305, which recognizes sialylated branched hexasaccharides (Piller et al., supra, (1991); Saitoh et al., supra, (1991)). Methods referred to in this example are described in greater detail in the examples that follow.

Following several rounds of transfection, one plasmid, pcDSRα-leu, directing high expression of the T305 antigen was identified. The cloned cDNA insert was isolated and sequenced, then compared with other reported sequences. The newly isolated cDNA sequence was nearly identical to the sequence reported for leukosialin, except the 5'-flanking sequences were different (Pallant et al., *Proc. Natl. Acad. Sci. USA* 86: 1328–1332 (1989), which is incorporated herein by reference).

Comparison of the cloned cDNA sequence with the genomic leukosialin DNA sequence revealed the start site of the cDNA sequence is located 259 bp upstream of the transcription start site of the previously reported sequence (FIG. 2; compare Exon 1' and Exon 1) (Shelley et al., *Biochem. J.* 270: 569–576 (1990); Kudo and Fukuda, *J. Biol. Chem.* 266: 8483–8489 (1991), which are incorporated herein by reference). A consensus splice site was identified at the exon-intron junction of the newly identified 122 bp exon 1' in pcDSRα-leu (Breathhath and Chambon, *Ann. Rev. Biochem.* 50: 349–383 (1981), which is incorporated herein by reference). This splice site is followed by the exon 2 sequence.

These results indicate the T305 antibody preferentially binds to branched hexasaccharides attached to leukosialin. Indeed, a small amount of the hexasaccharides (approximately 8% of the total) was detected in O-glycans isolated from control COS-1 cells. T305 binding is similar to anti-M and anti-N antibodies, which recognize both the glycan and polypeptide portions of erythrocyte glycoprotein, glycophorin (Sadlet et al., *J. Biol. Chem* 254: 2112–2119 (1979), which is incorporated herein by reference). These observations are consistent with reports that only leukosialin strongly reacted with T305 in Western blots of leukocyte cell extracts, even though leukocytes also express other glycoproteins, such as CD45, that must also contain the same hexasaccharides (Piller et al., supra, (1991); Saitoh et al., supra, (1991)).

EXAMPLE II

ESTABLISHMENT OF CHO CELL LINES THAT STABLY EXPRESS POLYOMA VIRUS LARGE T ANTIGEN AND LEUKOSIALIN

T305 preferentially binds to branched hexasaccharides attached to leukosialin. Such hexasaccharides are not present on the erythropoietin glycoprotein produced in CHO cells, although the glycoprotein does contain the precursor tetrasaccharide (Sasaki et al., *J. Biol. Chem.* 262: 12059–12076 (1987), which is incorporated herein by reference). T305 antigen also is not detectable in CHO cells transiently transfected with pcDSRα-leu. In order to screen for the presence of a cDNA clone expressing core 2 β1→6 N-acetylglucosaminyltransferase activity, a CHO cell line expressing both leukosialin and polyoma large T antigen was established (see, for example, Heffernan and Dennis *Nucl. Acids Res.* 19: 85–92 (1991), which is incorporated herein by reference).

Vectors: A plasmid vector, pPSVE1-PyE, which contains the polyoma virus early genes under the control of the SV40 early promoter, was constructed using a modification of the method of Muller et al., *Mol. Cell. Biol.* 4: 2406–2412 (1984), which is incorporated herein by reference. Plasmid pPSVE1 was prepared using pPSG4 (American Type Culture Collection 37337) and SV40 vital DNA (Bethesda Research laboratories) essentially as described by Featherstone et al., *Nucl. Acids Res.* 12: 7235–7249 (1984), which is incorporated herein by reference. Following EcoRI and HincII digestion of plasmid pPyLT-1 (American Type Culture Collection 41043), a DNA sequence containing the carboxy terminal coding region of polyomavirus large T antigen was isolated. The HincII site was converted to an EcoRI site by blunt-end ligation of phosphorylated EcoRI linkers (Stratagene). Plasmid pPSVE1-PyE was generated by inserting the carboxy-terminal coding sequence for large T antigen into the unique EcoRI site of plasmid pPSVE1.

Plasmid pZIPNEO-leu was constructed by introducing the EcoRI fragment of PEER-3 cDNA, which contains the complete coding sequence for human leukosialin, into the unique EcoRI site of plasmid pZIPNEO (Cepko et al., *Cell* 37: 1053–1063 (1984), which is incorporated herein by reference). Plasmid structures were confirmed by restriction mapping and by sequencing the construction sites. pZIP-NEO was kindly provided by Dr. Channing Der.

Transfection: CHODG44 cells were grown in 100 mm tissue culture plates. When the cells were 20% confluent, they were co-transfected with a 1:4 molar ratio of pZIPNEO-leu and pPSVE1-PyE using the calcium phosphate technique (Graham and van der Eb, *Virotogy* 52: 456–467 (1973), which is incorporated herein by reference). Transfected cells were isolated and maintained in medium containing 400 µg/ml G-418 (active drug).

Leukosialin expression: The total pool of G418-resistant transfectants has enriched for human leukosialin expressing cells by a one-step panning procedure using anti-leukosialin antibodies and goat anti-rabbit IgG coated panning dishes (Sigma) (Carlsson and Fukuda *J. Biol. Chem.* 61: 12779–12786 (1986), which is incorporated herein by reference). Clonal cell lines were obtained by limiting dilution. Six clonal cell lines expressing human leukosialin on the cell surface were identified by indirect immunofluorescence and isolated for further studies (Williams and Fukuda *J. Cell Biol.* 111: 955–966 (1990), which is incorporated herein by reference).

Polyoma virus-mediated replication: The ability of the six clonal cell lines to support polyoma virus large T antigen-mediated replication of plasmids was assessed by determining the methylation status of transfected plasmids containing a polyoma virus origin of replication (Muller at al., supra, 1984; Heffernan and Dennis, supra, 1991). Plasmid pGT/hCG contains a fused β1→4 galactosyltransferase and human chorionic gonadotropin α-chain DNA sequence inserted in plasmid pcDNAI, which contains a polyoma virus replication origin (Aoki et al., *Proc. Natl. Acad. Sci., USA* 89, 4319–4323 (1992), which is incorporated herein by reference).

Plasmid pGT/hCG was isolated from methylass-positive *E. coli* strain MC1061/P3 (Invitrogen), which methylates the adsnine residues in the DpnI recognition site, "GATC". The methylated Dpni recognition site is susceptible to cleavage by DpnI. In contrast, the DpnI recognition site of plasmids replicated in mammalian cells is not methylated and, therefore, is resistant to DpnI digestion.

Methylated plasmid pGT/hCG was transfected by lipofection into each of the six selected clonal cell lines expressing leukosialin. After 64 hr, low molecular plasmid DNA was isolated from the cells using the method of Hirt, *J. Mol. Biol.* 26: 365–369 (1967), which is incorporated herein by reference. Isolated plasmid DNA was digested with XhoI and DpnI (Stratagene), subjected to etectrophoresis in a 1% agarose gel, and transferred to nylon membranes (Micron Separations Inc., Mass.).

A 0.4 kb SmaI fragment of the β1→4 galactosyltransferase DNA sequence of pGT/hCG was radiolabeled with [$^{32}$P]dCTP using the random primer method (Feinberg and Vogelstein, *Anal. Biochem.* 132: 6–13 (1983), which is incorporated herein by reference). Hybridization was performed using methods well-known to those skilled in the art (see, for example, SamBrook et al., supra, (1989)). Following hybridization, the membranes were washed several times, including a final high stringency wash in 0.1×SSPE, 0.1% SDS for 1 hr at 65° C., then exposed to Kodak X-AR film at −70° C.

Figure 3A:
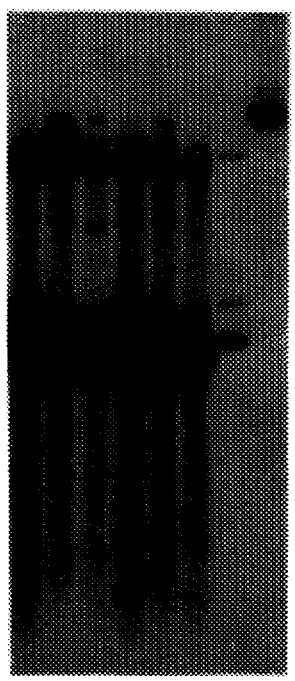
FIGS. 3A and B establish the ability of pGT/hCG to replicate in CHO cell lines expressing polyoma large T antigen and leukosialin.
Figure 3B:
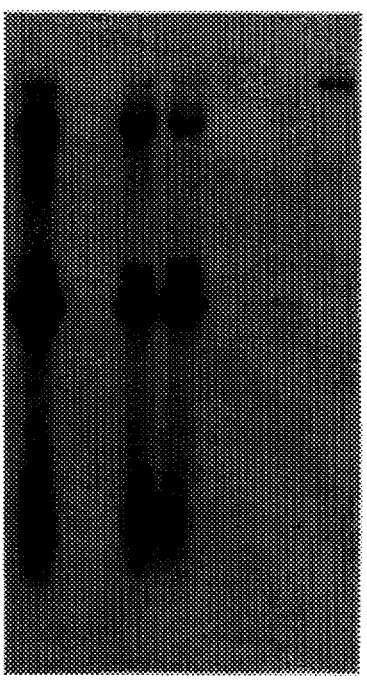
In FIG. 3B, replication of cell clone 5 (CHO-Py-leu), was further examined by treatment with increasing concentrations of DpnI and XhoI (lanes 2 and 3). Plasmid DNA isolated from MOP-8 cells was used as a control (lane 1). Plasmid DNA was extracted using the Hirt procedure and samples were digested with XhoI and DpnI. In parallel, pGT/hCG plasmid purified from E. coli MC1061/P3 was digested with XhoI and DpnI (lane 7 in FIG. 3A and lane 4 in FIG. 3B) or XhoI alone (lane 8 in FIG. 3A and lane 5 in FIG. 3B). The arrow indicates the migration of plasmid DNA resistant to DpnI digestion. The arrowheads indicate plasmid DNA digested by DpnI.
Figure 4A:
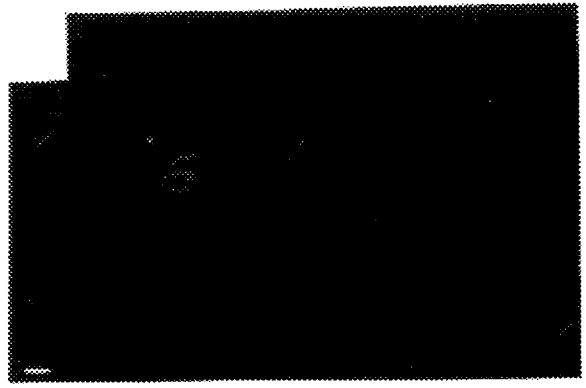
FIGS. 4A–D show the expression of T305 antigen expressed by pcDNAI-C2GnT. Subconfluent CHO-Py-leu cells were transfected with pcDNAI-C2GnT (FIG. 4A and FIG. 4B) or mock-transfected with pcDNAI (FIG. 4C and FIG. 4D). Sixty four hours after transfection, the cells were fixed, then incubated with mouse T305 monoclonal antibody followed by fluorescein isocyanate-conjugated sheep anti-mouse (FIGS. 4A, 4B and 4C). Two different areas are shown in FIGS. 4A and 4B.
Figure 4B:
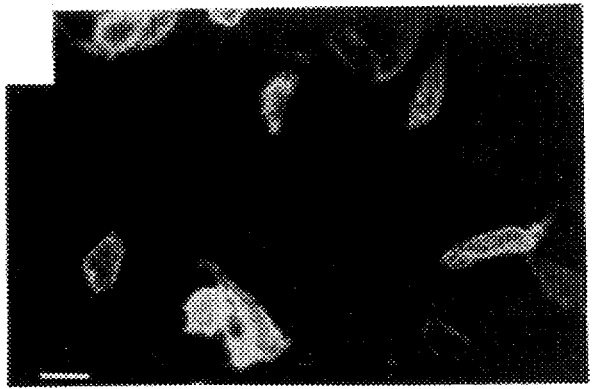
Figure 4C:
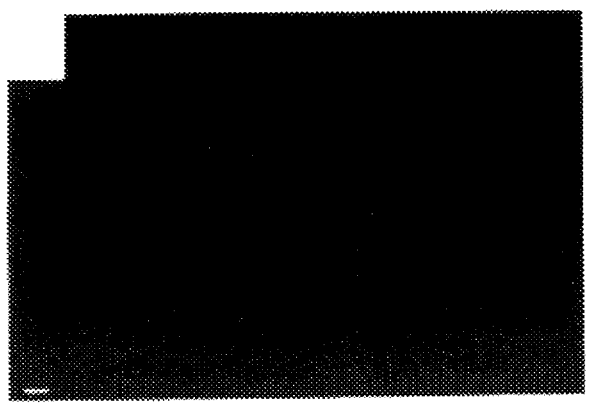
Figure 4D:
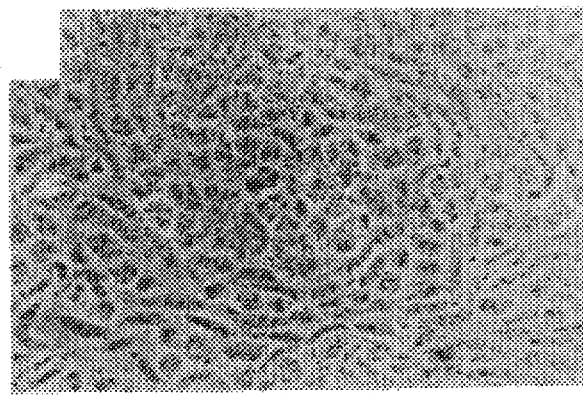

Four of the six clones tested supported replication of the pcDNAI-based plasmid, pGT/hCG (FIG. 3A., lanes 1, 3, 4 and 5). MOP-8 cells, a 3T3 cell line transformed by polyoma virus early genes (Muller et al., supra, (1984)), expresses endogenous core 2 β1→6 N-acetylglucosaminyltransferase activity and was used as a control for the replication assay (FIG. 3.B., lane 1). One clonal cell line that supported pGT/hCG replication, CHO-Py-leu (FIG. 3A., lane 5; FIG. 3B., lanes 2 and 3) and expressed a significant amount of leukosialin, was selected for further studies. pGT/hCG was kindly provided by Dr. Michiko Fukuda.

EXAMPLE III

ISOLATION OF A cDNA SEQUENCE DIRECTING EXPRESSION OF THE HEXASACCHARIDE ON LEUKOSIALIN

Poly(A)$^+$ RNA was isolated from HL-60 promyelocytes, which contain a significant amount of the core 2 β1→6 N-acetylglucosaminyltransferase (Saitoh et al., supra, (1991)). A cDNA expression library, pcDNAI-HL-60, was prepared (Invitrogen) and the library was screened for clones directing the expression of the T305 antigen.

Plasmid DNA from the pcDNAI-HL-60 cDNA library was transfected into CHO-Py-leu cells using a modification of the lipofection procedure, described below (Felgner et al., *Proc. Natl. Acad. Sci. USA* 84: 7413–7417 (1987), which is incorporated herein by reference). CHO-Py-leu cells were grown in 100 mm tissue culture plates. When the cells were 20% confluent, they were washed twice with Opti-MEM I (GIBCO). Fifty μg of lipofectin reagent (Bethesda Research Laboratories) and 20 μg of purified plasmid DNA were each diluted to 1.5 ml with Opti-MEM I, then mixed and added to the cells. After incubation for 6 hr at 37° C., the medium was removed, 10 ml of complete medium was added and incubation was continued for 16 hr at 37° C. The medium was then replaced with 10 ml of fresh medium.

Following a 64 hr period to allow transient expression of the transfected plasmids, the cells were detached in PBS/5 mM EDTA, pH7.4, for 30 min at 37° C., pooled, centrifuged and resuspended in cold PBS/10 mM EDTA/5% fetal calf serum, pH7.4, containing a 1:200 dilution of ascites fluid containing T305 monoclonal antibody. The cells were incubated on ice for 1 hr, then washed in the same buffer and panned on dishes coated with goat anti-mouse IgG (Sigma) (Wysocki and Sato *Proc. Natl. Acad. Sci. USA* 75: 2844–2848 (1978); Seed & Aruffo *Proc. Natl. Acad. Sci. USA* 84: 3365–3369 (1987), which are incorporated herein by reference). T305 monoclonal antibody was kindly provided by Dr. R. L. Fox, Scripps Research Foundation, La Jolla, Calif.

Plasmid DNA was recovered from adherent cells by the method of Hirt, supra, (1967), treated with DpnI to eliminate plasmids that had not replicated in transfected cells, and transformed into *E. coli* strain MC1061/P3. Plasmid DNA was then recovered and subjected to a second round of screening. *E. coil* transformants containing plasmids recovered from this second enrichment were plated to yield 8 pools of approximately 500 colonies each. Replica plates were prepared using methods well-known to those skilled in the art (see, for example, Serook et al., supra, (1989)).

The pooled plasmid DNA was prepared from replica plates and transfected into CHO-Py-leu cells. The transfectants were screened by panning. One plasmid pool was selected and subjected to three subsequent rounds of selection. One plasmid, pcDNAI-C2GnT, which directed the expression of the T305 antigen, was isolated. CHO-Py-leu cells transfected with pcDNAI-C2GnT express the antigen recognized by T305, whereas CHO-Py-leu cells transfected with pcDNAI are negative for T305 antigen FIGS. 4A–D. These results show pcDNAI-C2GnT directs the expression of a new determinant on leukosialin that is recognized by T305 monoclonal antibody. This determinant is the branched hexasaccharide sequence, NeuNAcα2→3Galβ1→3 (NeuNAcα2→3Galβ1→4 GlcNAcβ1→6)GalNAc.

EXAMPLE IV

CHARACTERIZATION OF C2GnT

DNA sequence: The cDNA insert in plasmid pcDNAI-C2GnT was sequenced by the dideoxy chain termination method using Sequenase version 2 reagents (United States Biochemicals) (Sanger et al., *Proc. Natl. Acad. Sci. USA* 74: 5463–5467 (1977), which is incorporated herein by reference). Both strands were sequenced using 17-mer synthetic oligonucleotides, which were synthesized as the sequence of the cDNA insert became known.

Plasmid pcDNAI-C2GnT contains a 2105 base pair insert (FIG. 5). The cDNA sequence ends 1878 bp downstream of the putative translation start site. A polyadenylation signal is present at nucleotides 1694–1699. The significance of the large number of nucleotides between the polyadenylation signal and the beginning of the polyadenyl chain is not clear. However, this sequence is A/T rich.

Deduced amino acid sequence: The cDNA insert in plasmid pcDNAI-C2GnT encodes a single open reading frame in the sense orientation with respect to the pcDNAI promoter (FIG. 5). The open reading frame encodes a putative 428 amino acid protein having a molecular mass of 49,798 daltons.

Hydropathy analysis indicates the predicted protein is a type II transmembrane molecule, as are all previously reported mammalian glycosyltransferases (Schachter, supra, (1991)). In this topology, a nine acid cytoplasmic NH$_2$-terminal segment is followed by a 23 amino acid transmembrane domain flanked by basic amino acid residues. The large COOH-terminus consists of the stem and catalytic domains and presumably faces the lumen of the Golgi complex.

The putative protein contains three potential N-glycosylation sites (FIG. 5, asterisks). However, one of these sites contains a proline residue adjacent to asparagine and is not likely utilized in vivo.

No matches were obtained when the C2GnT cDNA sequence and deduced amino acid sequence were compared with sequences listed in the PC/Gene 6.6 data bank. In particular, no homology was revealed between the deduced amino acid sequence of C2GnT and other glycosyltransferases, including N-acetylglucosaminyltransferase I (Sarkar et al., *Proc. Natl. Acad. Sci. USA* 88: 234–238 (1991), which is incorporated herein by reference).

mRNA expression: Poly(A)$^+$ RNA was prepared using a kit (Stratagene) and resolved by electrophoresis on a 1.2% agarose/2.2M formaldehyde gel, and transferred to nylon membranes (Micro Separations Inc., Mass.) using methods well-known to those skilled in the art (see, for example, Sambrook et al., supra, (1989)). Membranes were probed using the EcoRI insert of pPROTA-C2GnT (see below) radiolabeled with [$^{32}$P]dCTP by the random priming method (Feinberg and Vogelstein, supra, (1983). Hybridization was performed in buffers containing 50% formamide for 24 hr at 42° C. (Sambrook et al., supra, (1989)). Following hybridization, filters were washed several times in 0.1xSSPE/0.1% SDS at room temperature and once in 0.1xSSPE/0.1% SDS at 42° C., then exposed to Kodak X-AR film at –70° C.

Figure 6:
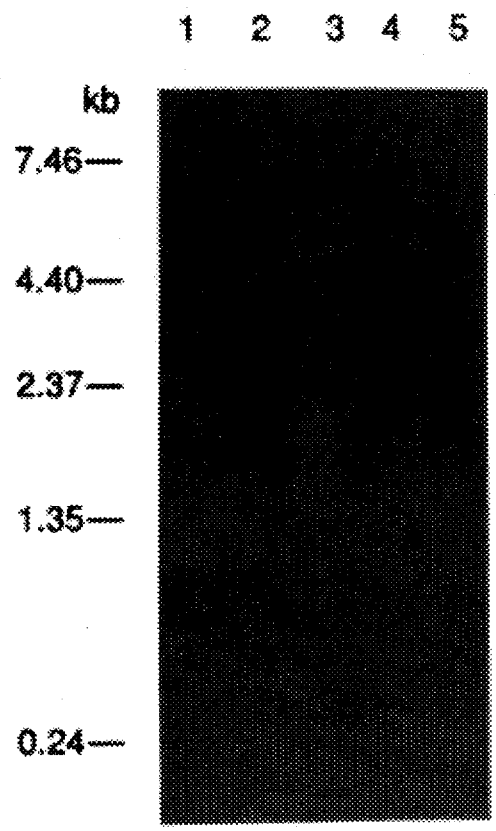
FIG. 6 shows the expression of core 2 β1→6 N-acetylglucosaminyltransferase mRNA in various cell types. Poly(A)⁺ RNA (11 μg) from CHO-Py-leu cells (lane 1), EL-60 promyelocytes (lane 2), K562 erythrocytic cells (lane 3), and SP and L4 colonic carcinoma cells (lanes 4 and 5) was resolved by electrophoresis. RNA was transferred to a nylon membrane and hybridized with a radiolabeled fragment of pPROTA-C2GnT. Migration of RNA size markers is indicated.

FIG. 6 compares the level of core 2 β1→6 N-acetylglucosaminyltransferase mRNA isolated from HL-60 promyelocytes, K562 erythroleukemia cells, and poorly metastatic SP and highly metastatic L4 colonic carcinoma cells. The major RNA species migrates at a size essentially identical to the ~2.1 kb C2GnT cDNA sequence. The same result is observed for HL-60 cells and the two colonic cell lines, which apparently synthesize the hexasaccharides. In addition, two transcripts of ~3.3 kb and 5.4 kb in size were detected in these cell lines. The two larger transcripts may result from differential usage of polyadenylation signals.

No hybridization occurred with poly(A)$^+$ RNA isolated from K562 cells, which lack the hexasaccharide, but synthesize the tetrasaccharide (Carlsson et al., supra, (1986)), which is incorporated herein by reference. Similarly, no hybridization was observed for poly(A)$^+$ RNA isolated from CHO-Py-leu cells (FIG. 6, lane 1).

EXAMPLE V

EXPRESSION OF ENZYMATICALLY ACTIVE β1→6 N-ACETYLGLUCOSAMINYLTRANSFERASE

In order to confirm that C2GnT cDNA encodes for core 2 β1→6 N-acetylglucosaminyltransferase, enzymatic activity was examined in CHO-Py-leu cells transfected with pcDNAI or pcDNAI-C2GnT. Following a 64 hr period to allow transient expression, cell lysates were prepared and core 2 β1→6 N-acetylglucosaminyltransferase activity was measured.

N-acetylglucosaminyltransferase assays were performed essentially as described by Saitoh et al., supra, (1991), Yousefi et al., supra, (1991), and Lee et al., *J. Biol. Chem.* 265: 20476–20487 (1990), which is incorporated herein by reference. Each reaction contained 50 mM MES, pH7.0, 0.5 μCi of UDP-{$^3$H}GlcNAc in 1 mMUDP-GlcNAc, 0.1M GlcNAc, 10 mM Na$_2$EDTA, 1 mM of acceptor and 25 μl of either cell lysate, cell supernatant or IgG-Sepharose matrix in a total reaction volume of 50 μl.

Reactions were incubated for 1 hr at 37° C., then processed by C18 Sep-Pak chromatography (Waters) (Palcic et al., *J. Biol. Chem.* 265: 6759–6769 (1990), which is incorporated herein by reference). Core 2 and core 4 β1→6 N-acetylglucosaminyltransferase were assayed using the acceptors p-nitrophenyl Galβ1→3GalNAc and p-nitrophenyl GlcNAcβ1→3GalNAc, respectively (Toronto Research Chemicals).

UDP-GlcNAc: α-Man β1→6 N-acetylglucosaminyltransferase(V) was assayed using the acceptor GlcNAcβ1→2Manα1→6Glc-β-O-(CH$_2$)$_7$CH$_3$. The blood group I enzyme, UDP-GlcNAc: GlcNAcβ1→3Galβ1→4GlcNAc (GlcNAc to Gal) β1→6 N-acetylglucosaminyltransferase, was assayed using GlcNAcβ1→3Galβ1→4GlcNAcβ1→6Manα1→6Manβ1→O-(CH$_2$)$_8$COOCH$_3$ or Galβ1→4GlcNAcβ1→3Galβ1→4GlcNAcβ1→3Galβ1→4GlcNAcβ1→O-(CH$_2$)$_7$CH$_3$ as acceptors (Gu et al., *J. Biol. Chem.* 267: 2994–2999 (1992), which is incorporated herein by reference). Synthetic acceptors were kindly provided by Dr. Olé Hindsgaul, University of Alberta, Canada.

Results of the c2GnT assay is shown in Table I. Assuming transfection efficiency of the cells is approximately 20–30%, the level of enzymatic activity directed by cells transfected with pcDNAI-C2GnT is roughly equivalent to the level observed in HL-60 cells.

TABLE I

Core 2 β1→6 N-acetylglucosaminyltransferase activity in CHO-Py-Leu cell extracts transfected with pcDNAI or pcDNAI-C2GnT.

| Vector | Core 2 β1→6 GlcNAc transferase activity (pmol/mg of protein/hr) |
|---|---|
| pcDNAI | n.d. |
| pcDNAI-C2GnT | 764 |

CHO-Py-leu cells were transfected with pcDNAI or pcDNAI-C2GnT, as described in the specification. Endogenous activity was measured in the absence of acceptor and subtracted from values determined in the presence of added acceptor. GalB1→3GalNAcα-p-nitrophenyl was used as an acceptor. n.d. = not detectable. For comparison, the core 2 β1→6 N-acetylglucosaminyltransferase activity measured in HL-60 cells under identical conditions was 3228 pmol/mg of protein per hr.

Figure 7:
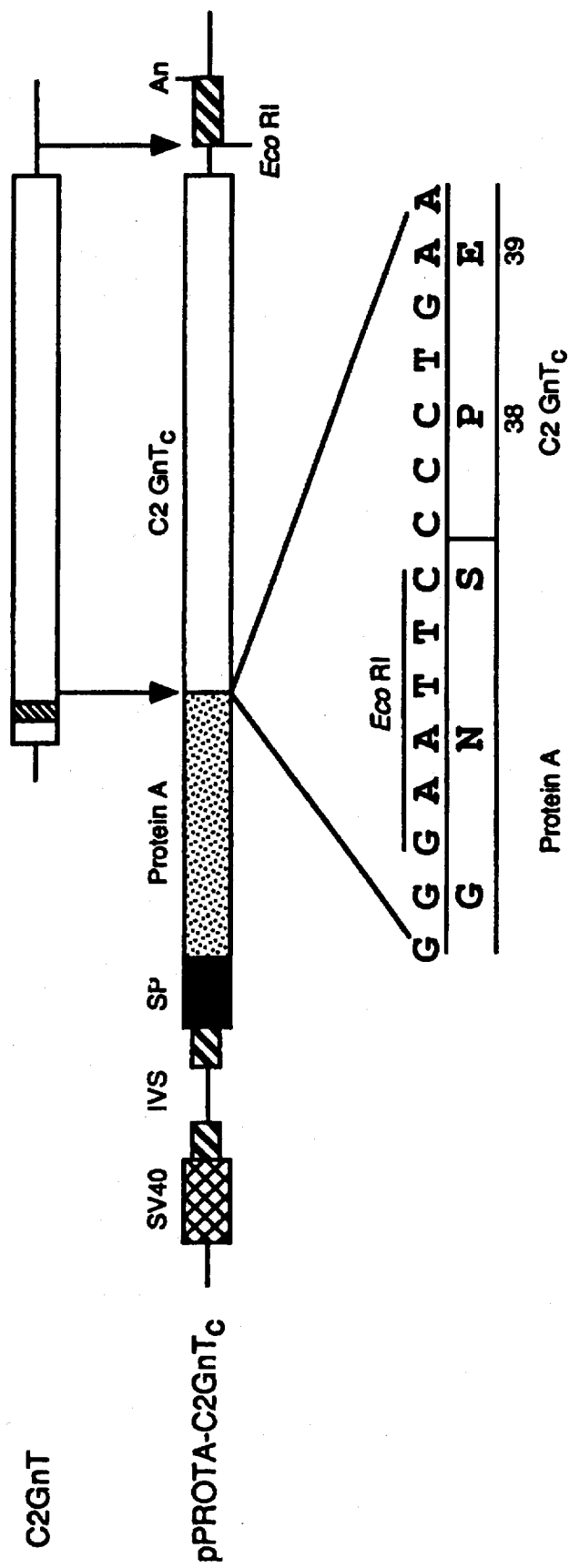
FIG. 7 illustrates the construction of the vector encoding the protein A-C2GnT fusion protein. The cDNA sequence corresponding to Pro[38] to His[428] was fused in frame with the IgG binding domain of S. aureus protein A (bottom; SEQ. ID. NO. 6). The sequence includes the cleavable signal peptide, which allows secretion of the fused protein. The coding sequence is under control of the SV40 promoter. The remainder of the vector sequence shown was derived from rabbit β-globin gene sequences, including an intervening sequence (IVS) and a polyadenylation signal (An).

In order to unequivocally establish that C2GnT cDNA sequence encodes core 2 β1→6 N-acetylglucosaminyltransferase, plasmid, pPROTA-C2GnT was constructed containing the DNA sequence encoding the putative catalytic domain of core 2 β1→6 N-acetylglucosaminyltransferase fused in frame with the signal peptide and IgG binding domain of *S. aureus* protein A (FIG. 7). The putative catalytic domain is contained in a 1330 bp fragment of the C2GnT cDNA that encodes amino acid residues 38 to 428. Plasmid pPROTA was kindly provided by Dr. John B. Lowe.

The polymerase chain reaction (PCR) was used to insert EcoRI recognition sites on either side of the 1330 bp sequence in pcDNAI-C2GnT DNA. PCR was performed using the synthetic oligonucleotide primers 5'-TTTGAATTCCCCTGAATTTGTAAGTGTCAGACAC-3' (SEQ. ID. NO. 6) and 5'-TTTGAATTCGCAGAAACCATGCAGCTTCTCTGA-3' (SEQ. ID. NO. 7) (EcoRI recognition sites underlined). The EcoRI sites allowed direct, in-frame insertion of the fragment into the unique EcoRI site of plasmid pPROTA (Sanchez-Lopez et al., *J. Biol. Chem.* 263: 11892–11899 (1988), which is incorporated herein by reference).

The nucleotide sequence of the insert as well as the proper orientation were confirmed by DNA sequencing using the primers described above for cDNA sequencing. Plasmid pPROTA-C2GnT allows secretion of the fusion protein from transfected cells and binding of the secreted fusion protein by insolubilized immunoglobulins.

Either pPROTA or pPROTA-C2GnT was transfected into COS-1 cells. Following a 64 hr period to allow transient expression, cell supernatants were collected (Kukowska-Latallo et al., supra, (1990)). Cell supernatants were cleared by centrifugation, adjusted to 0.05% Tween 20 and either assayed directly for core 2 β1→6 N-acetylglucosaminyltransferase activity or used in IgG-Sepharose (Pharmacia) binding studies. For the latter assay, supernatants (10 ml) were incubated batchwise with approximately 300 μl of IgG-Sepharose for 4 hr at 4° C. The matrices were then extensively washed and used directly for glycosyltransferase assays.

No core 2 β1→6 N-acetylglucosaminyltransferase activity was detected in the medium of COS-1 cells transfected with the control plasmid, pPROTA. Similarly, no enzymatic activity was associated with IgG-Sepharose beads. In contrast, a significant level of core 2 β1→6 N-acetylglucosaminyltransferase activity was detected in the medium of COS-1 cells transfected with pPROTA-C2GnT. The activity also associated with the IgG-Sepharose beads (Table II). No activity was detected in the supernatant following incubation of the supernatant with IgG-Sepharose.

TABLE II

Determination of Enzymatic Activities Directed by pPROTA-C2GnT.

| Acceptors and linkages formed | Radioactivity (cpm) with (+) and without (−) acceptor | |
|---|---|---|
| | − | + |
| GlcNAcβ1↘6<br>Galβ1⟶3GalNAc<br>(core 2-GnT) | 109 | 1048 |
| GlcNAcβ1↘6<br>GlcNAcβ1⟶3GalNAc<br>(core 4-GnT) | 111 | 113 |
| GlcNAcβ1↘6<br>GlcNAcβ1⟶2Man<br>(GnTV) | 118 | 115 |
| GlcNAcβ1↘6<br>GlcNAcβ1⟶3Gal<br>(I-GnT) | 111 | 113 |
| GlcNAcβ1↘6<br>Galβ1⟶4GlcNAcβ1⟶3Gal<br>(I-GnT) | 99 | 96 |

COS-1 cells were transfected with pPROTA-C2GnT and the conditioned media were incubated with IgG-Sepharose. The proteins bound to the IgG-Sepharose were assayed for β1→6 N-acetylglucosaminyltransferase activity by using appropriate acceptors. The linkages formed are indicated by italics. Similar results were obtained in three independent experiments.

EXAMPLE VI

DETERMINATION OF C2GnT SPECIFICITY

Four types of β1→6 N-acetylglucosaminyltransferase linkages have been reported, including core 2 and core 4 in O-glycans, I-antigen and a branch attached to mannose that forms tetraantennary N-glycans (see Table II). In order to determine whether these different structures are also synthesized by the cloned C2GnT cDNA sequence, enzymatic activity was determined using five different acceptors.

As shown in Table II, the fusion protein was only active with the acceptor for core 2 formation. The same was true when the formation of β1→6 N-acetylglucosaminyl linkage to internal galactose residues was examined (Table II, see structure at bottom). This result precludes the likelihood that the enzyme encoded by the C2GnT cDNA sequence may add N-acetylglucosamine to a non-reducing terminal galactose. The HI-60 core 2 β1→6 N-acetylglucosaminyltransferase is exclusively responsible for the formation of the GlcNAcβ1→6 branch on Galβ1→3 GalNAc.

Although the invention has been described with reference to the disclosed embodiments, it should be understood that various modifications can be made without departing from the spirit of the invention. Accordingly, the invention is limited only by the following claims.

We claim:

1. An isolated antibody or an antigen binding antibody fragment having specific reactivity for human core 2 β1→6 N-acetylglucosaminyltransferase having activity for a core 1-containing acceptor molecule.

2. The antibody of claim 1, which is a monoclonal antibody.

3. A cell line producing the antibody of claim 1.

4. The cell line of claim 3, which is a hybridoma cell line.

* * * * *

UNITED STATES PATENT AND TRADEMARK OFFICE
CERTIFICATE OF CORRECTION

PATENT NO. : 5,684,134
DATED : November 4, 1997
INVENTOR(S) : Fukuda et al.

Page 1 of 2

It is certified that error appears in the above-identified patent and that said Letters Patent is hereby corrected as shown below:

Title page, Item [54], and Column 1, line 2,
"ACETYLGLUCOSAMININYLTRANSFERASE" and replace with -- ACETYLGLUCOSAMINYLTRANSFERASE --.

Column 1,
Line 52, please delete "(19911)" and replace with -- (1991) --.

Column 2,
Line 1, please delete "135 kna" and replace with -- 135 kDa --.

Column 3,
Line 46, please delete "N-acetylgiucosaminyttransferase" and replace with -- N-acetylglucosaminyltransferase --.

Column 4,
Line 28, please delete "(SEQ. In." and replace with -- (SEQ. ID. --.

Column 5,
Line 64, please delete "OHO cells" and replace with -- CHO cells --.

Column 6,
Line 12, please delete "C2GmT" and replace with -- C2GnT --.

Column 8,
Line 16, please delete "Serook" and replace with -- Sambrook --.
Line 43, please delete "N-acetylgiucosaminyttransferase" and replace with -- N-acetylglucosaminyltransferase --.

Column 9,
Line 52, please delete "pcDSRG." and replace with -- pcDSRα. --.

Column 10,
Line 3, please delete "gone" and replace with -- gene --.
Line 4, please delete "gone" and replace with -- gene --.

Column 11,
Line 30, please delete "(Breathhath" and replace with -- (Breathnath --.
Line 41, please delete "(Sadlet" and replace with -- (Sadler --.

UNITED STATES PATENT AND TRADEMARK OFFICE
CERTIFICATE OF CORRECTION

PATENT NO.   : 5,684,134
DATED        : November 4, 1997
INVENTOR(S)  : Fukuda et al.

It is certified that error appears in the above-identified patent and that said Letters Patent is hereby corrected as shown below:

Column 12,
Line 10, please delete "laboratories)" and replace with -- Laboratories) --.
Line 33, please delete "*Virotogy*" and replace with -- *Virology* --.
Line 41, please delete "*Chem.* 61:" and replace with -- *Chem.* 261: --.
Line 61, please delete "methylass-positive" and replace with -- methylase-positive --.
Line 63, please delete "adsnine" and replace with -- adenine --.
Line 64, please delete "Dpni" and replace with -- DpnI --.

Column 13,
Line 7, please delete "etectrophoresis" and replace with -- electrophoresis --.
Line 16, please delete "SamBrook" and replace with -- Sambrook --.

Column 14,
Line 15, please delete "Serook" and replace with -- Sambrook --.
Line 53, please delete "49,798" and replace with -- 49,790 --.
Line 58, please delete "nine acid" and replace with -- nine amino acid --.

Column 15,
Line 62, please delete "1 mMUDP-GlcNac," and replace with -- 1 mMUDP-GlcNac --.

Column 16,
Line 20, please delete "c2GnT" and replace with -- C2GnT --.

Column 18,
Line 52, please delete "HI-60" and replace with -- HL-60 --.

Signed and Sealed this

Twenty-fifth Day of December, 2001

*Attest:*

JAMES E. ROGAN
*Attesting Officer*   *Director of the United States Patent and Trademark Office*